United States Patent
De Castro et al.

[11] Patent Number: 5,841,021
[45] Date of Patent: Nov. 24, 1998

[54] SOLID STATE GAS SENSOR AND FILTER ASSEMBLY

[76] Inventors: Emory S. De Castro, 60 Little Nahant Rd., Nahant, Mass. 01908-1028; J. David Genders, 1299 Two Rod Rd., Marilla, N.Y. 14102; Norman L. Weinberg, 95 Chasewood La., East Amherst, N.Y. 14051

[21] Appl. No.: 523,687

[22] Filed: Sep. 5, 1995

[51] Int. Cl.⁶ .............................. G01N 27/16; H01L 7/00; B32B 5/00
[52] U.S. Cl. .................. 73/23.2; 73/31.02; 73/31.06; 73/23.31; 422/98; 422/94; 340/34; 340/633; 238/34; 204/424; 204/431
[58] Field of Search .................. 73/23.2, 31.06, 73/23.4, 25.04, 25.29; 340/634; 324/71.5, 439; 422/98, 90, 94, 83; 204/412, 421, 424, 425, 426, 431, 427; 338/34, 224

[56] References Cited

U.S. PATENT DOCUMENTS

| | | | |
|---|---|---|---|
| 3,793,158 | 2/1974 | Hamilton | 204/1 T |
| 3,864,628 | 2/1975 | Klass et al. | 324/71 SN |
| 3,880,722 | 4/1975 | Beltzer | 204/1 T |
| 4,025,412 | 5/1977 | LaConti | 204/195 R |
| 4,171,253 | 10/1979 | Nolan et al. | 204/195 S |
| 4,227,984 | 10/1980 | Dempsey et al. | 204/195 S |
| 4,240,799 | 12/1980 | Ryerson | 23/232 E |
| 4,369,647 | 1/1983 | Shigemori et al. | 73/27 R |
| 4,443,793 | 4/1984 | Hall, Jr. | 340/634 |
| 4,580,439 | 4/1986 | Manaka | 73/23 |
| 4,584,867 | 4/1986 | Forster | 73/23 |
| 4,587,104 | 5/1986 | Yannopoulos | 422/94 |
| 4,644,333 | 2/1987 | Barendsz et al. | 340/634 |
| 4,718,991 | 1/1988 | Yamazoe et al. | 204/1 T |
| 4,776,203 | 10/1988 | Jones et al. | 73/23 |
| 4,792,433 | 12/1988 | Katsura et al. | 422/98 |
| 4,836,907 | 6/1989 | Pederson | 204/412 |
| 4,876,115 | 10/1989 | Raistrick | 427/115 |
| 4,887,455 | 12/1989 | Payne et al. | 73/27 R |
| 4,893,108 | 1/1990 | Kolesar, Jr. | 338/34 |
| 4,911,892 | 3/1990 | Grace et al. | 422/94 |
| 4,916,935 | 4/1990 | Novack et al. | 73/27 R |
| 5,019,263 | 5/1991 | Haag et al. | 210/500.25 |
| 5,055,266 | 10/1991 | Stetter et al. | 422/83 |
| 5,069,794 | 12/1991 | Haag et al. | 210/650 |
| 5,104,425 | 4/1992 | Rao et al. | 55/16 |
| 5,133,857 | 7/1992 | Alberti et al. | 204/425 |
| 5,173,166 | 12/1992 | Tomantschger et al. | 204/412 |
| 5,186,810 | 2/1993 | Nagai et al. | 204/425 |
| 5,238,729 | 8/1993 | Debe | 428/245 |
| 5,302,274 | 4/1994 | Tomantschger et al. | 204/412 |
| 5,331,310 | 7/1994 | Stetter et al. | 340/632 |
| 5,332,424 | 7/1994 | Rao et al. | 95/47 |
| 5,650,054 | 7/1997 | Shen et al. | 204/412 |

FOREIGN PATENT DOCUMENTS

| | | |
|---|---|---|
| 0575628 | 8/1993 | European Pat. Off. . |
| 0563851 | 10/1993 | European Pat. Off. . |
| 563974 A1 | 10/1993 | Germany . |
| 8809500 | 12/1988 | WIPO . |

*Primary Examiner*—Hezron E. Williams
*Assistant Examiner*—J. David Wiggins
*Attorney, Agent, or Firm*—Howard M. Cohn

[57] ABSTRACT

An electrochemical gas sensor is provided, the use of which permits quantitative measurement of volatile gas contaminants in an atmosphere being monitored, generally at ambient temperatures below 100° C. The sensor is constructed of a sensor electrode and a reference electrode on a separator in such a manner as to be exposed to the atmosphere which is sensed for gaseous contaminants. In an alternative embodiment, the sensors can be covered with a selective filter which will selectively allow only small molecule toxic gases to pass for sensing by the sensor electrode while excluding larger interfering gas molecules. In another alternative embodiment, a multiple layer electrochemical gas sensor detects the presence of volatile gas contaminants in a sample gas as well as humidity, temperature, and/or pressure of the gas sample.

121 Claims, 20 Drawing Sheets

SOLID STATE GAS SENSOR AND FILTER ASSEMBLY

FIELD OF THE INVENTION

This invention relates to electrochemical gas sensors. In particular, the invention relates to gas sensors which sense the presence of a gas contaminant in an atmosphere, especially in instances where the temperature of the atmosphere is below about 100° C. The electrochemical gas sensor has a specific potential developed between a sensor electrode and a reference electrode, which potential will be indicative of the amount of the gas contaminant that is present. The present invention also includes membrane filters whose use with the gas sensors makes them selective and particularly effective. Further, the invention covers electrochemical gas sensors capable of both being selective for contaminants and having automatic compensation for changes in environmental variables such as temperature and humidity.

BACKGROUND OF THE INVENTION

In inhabited environments, and in environments where other dangers such as explosion, fire or toxicity may occur, there is very often a requirement to test for gas contaminants which may create a potential hazard. In particular, there is an increasing demand for devices to monitor a specific atmosphere, generally an enclosed volume for toxic or flammable gases. Also, particularly where the atmosphere being monitored is inhabited by humans, there is a specific requirement for sensors having a rapid and reliable response to such contaminating gases as carbon monoxide, oxides of nitrogen, sulfur dioxide, hydrogen sulphide, carbon dioxide, hydrogen, phosphine, arsine, methanol, volatile hydrocarbons, and so on. Any such gas requires a specific sensor cell design which is reactive to the presence of the specific contaminating gases being tested.

In some circumstances, the enclosed volume being monitored may be monitored only for one or two specific contaminating gases, which gases are the only likely gas contaminants to occur in the atmosphere being monitored. An example may be storage rooms where hazardous chemicals may be kept, or production facilities where hazardous materials are being released or are being used in the manufacture of other materials, where the possible gas contaminants are known and specific cell systems may thereby be designed.

To satisfy the requirement to be able to monitor for the presence of gas contaminants, it is necessary not only that sensor cells be provided that are capable of being economically produced and therefore readily purchased, it is also necessary that such sensor cells shall have a reasonably long active lifetime when installed for use, even of many years. Moreover, particularly where it is necessary to monitor for toxic or flammable gases where there may be humans in the environment being monitored, or where there is a specific hazard, such sensor cells must be capable of detecting the presence of low concentrations of contaminant gases being tested for, so as to provide sufficient warning before the concentration of contaminant gas reaches dangerous levels.

There is an ever increasing demand for devices to monitor the environment including toxic and flammable gases in the atmosphere. In order to maintain the low level of such gases essential in a human inhabited environment, sensors with a rapid and reliable response to toxic/flammable gas levels below 500 ppm are sought. Sensors for gases as diverse as carbon monoxide, oxides of nitrogen, sulfur dioxide, hydrogen sulfide, carbon dioxide, hydrogen, methanol, ethanol, hydrocarbons, etc. are all in demand.

Gas quality monitors can already be found in the industrial workplace, auto repair shops, parking garages, commercial buildings, hospitals, mines, ships, submarines, and airplanes. Currently, awareness of the dangers of carbon monoxide poisoning in the home have spurred the development of consumer carbon monoxide alarms. In general, these sensing devices are expensive and some are unreliable. Using the example of a carbon monoxide sensor, a device similar in size and cost to commercially available smoke detectors would have considerable market potential in places where combustion takes place, such as for example, ramp garages, police cars used for winter stake-outs, residential dwellings heated by kerosene, wood burning stoves or other combustibles, or in monitoring any process producing toxic gases as a byproduct.

Electrochemical cells are readily miniaturized, requiring only low power circuitry, and the output can always be easily and cheaply converted to a voltage to activate a warning device or displayed in digital or analog form. Moreover, most gases of interest in atmospheric monitoring (e.g. oxygen, chlorine, carbon monoxide, carbon dioxide, oxides of nitrogen, sulfur dioxide, hydrogen, alcohol, etc) are all electroactive under some conditions. Hence, electrochemical cells are frequently selected as the sensing element in small and/or portable monitoring devices. Prior art devices have included various patented devices such as those described below, and may generally be defined as comprising electrochemical sensors, ionization chamber sensors, photoelectric types of sensors, and metal oxide semiconductor devices. Most prior art sensors are solid state or solid electrolyte, and may employ stabilized zirconia, or zirconia-yttria and tin oxides. However, it is believed that any sensor heretofore used for monitoring and/or controlling gas atmospheres has exhibited one or more of the following disadvantageous characteristics: (1) they often have quite complex structures; (b) they very often must operate or can only operate at elevated temperatures (e.g. from 150° C. to 600° C.); (c) as well as or as a consequence of the above, they may require outside sources of electrical energy and/or heat to maintain their operating temperatures; (d) such devices may have long start-up or warm-up periods before reaching their operating characteristics; (e) nearly all prior art devices are costly to build and/or to operate; and finally, (f) the prior art devices are subject to deterioration over time, due to gas poisoning, accumulation, or reaction with their sensing systems and/or sensing elements.

The prior art ambient gas sensors are normally based on aqueous electrolytes. The gases from the atmosphere to be monitored generally enter the cell of the sensor by diffusion through a gas permeable membrane or a porous structure. From the viewpoint of signal measurement, there are three types of electrochemical sensors: amperometric sensors, conductometric sensors, and potentiometric sensors.

With amperometric sensors, the current for the oxidation/reduction of a gas is monitored at a predetermined or applied potential. Usually this potential is chosen so that the current is determined by the diffusion of the gas into the cell. These devices often have three electrodes: a working or sensing electrode where the reaction of interest occurs, a counter electrode to provide a current loop with the working electrode, and a reference electrode to provide a constant voltage source in order to control the working electrode's potential. Some designs combine the functions of the reference and counter electrode into one element. Amperometric sensors are also called "potentiostatic" referring to holding a potential constant and monitoring the current, or "galvanic" which are closer in operation to a battery or fuel cell whereby the current developed by consuming the analyte and a reference gas is measured. Such sensors are available for oxygen, chlorine, carbon monoxide, and sulfur dioxide.

Several examples of specific amperometric prior art gas sensing elements or cells and their deficiencies are next discussed.

U.S. Pat. No. 5,331,310 to Pan et al. describes an amperometric carbon monoxide (CO) sensor based on oxidizing carbon monoxide using three electrodes, whereby the function of the reference and counter electrode are combined into one. Sulfuric acid is used as an electrolyte and the sensor is designed to avoid the water loss associated with using aqueous electrolytes. Importantly, the electrodes are deposited on the surface of a water insoluble solid ionic conductor, i.e., an ion exchange membrane. To make the device selective for carbon monoxide but insensitive to an interference such as isopropyl alcohol, a carbon filter filled with a permanganate salt is incorporated in the device. The latter filter is a chemically reactive layer that selectively reacts with components other than CO. As in any amperometric sensor, the constant drain of current to operate the device limits its useful time of operation. If the electrode area is reduced in size to decrease the current drain, then the signal for CO decreases.

U.S. Pat. No. 4,718,991 to Yamazoe et al. describes an amperometric proton conductor gas sensor which avoids liquid electrolytes by bonding electrodes to a layer of material that allows for ionic conductivity of one of the ions. In this device, protons are mobile while negatively charged groups are immobilized in the membrane. Cited membrane materials include Nafion®, zirconia phosphate, antimonic acid, dodecylhydrophosphoric acid, and uranyl hydrogen phosphate tetrahydrate. This is an amperometric device where the migration of the protons through the membrane provide the ionic conduction needed to support the electronic conduction, i.e., the electrochemical reactions at the working and counter electrodes. Since the reference material must be gas-impermeable to keep a constant potential, the reference must be isolated from the contaminant gas. The resulting assembly is very expensive to produce, even in quantities.

U.S. Pat. No. 4,227,984 to Dempsey et al. and U.S. Pat. No. 4,025,412 to LaConti disclose amperometric, potentiostated, three-electrode, solid polymer electrolyte (SPE) gas sensors which use Nafion® as the room temperature, solid state electrolyte. These amperometric devices use electrodes as integral parts of the Nafion® membrane, as well as an enclosed reference electrode chamber filled with hydrogen. A reservoir with distilled water is added to maintain constant humidity in the cell. No provision is made to insure that the sensor (working) electrode will be insensitive to interferences such as isopropyl alcohol. Ultimately, these sensor are limited by the hydrogen supply and the integrity of the hydrogen gas seal.

U.S. Pat. No. 5,133,857 to Alberti et al. describes an amperometric type, solid-state sensor relying primarily on nonorganic type room temperature proton conductors, i.e., uranyl hydrogen phosphate, antimonic acid, phosphomolybdic acid, zirconium hydrogen phosphate, or organic polymers containing acidic groups. A sandwich type apparatus is described with a catalytic platinum electrode on one side of the assembly, and a reference and auxiliary (also called a counter electrode) electrode on the other side. The signal is obtained when the auxiliary electrode is supplied with a current or voltage impulse using a power feed system, and a potential of the reference electrode versus the catalytic electrode is measured after each of the impulses using a measuring system. As with the other amperometric type sensors, a specific voltage must be applied and maintained to operate the sensor.

U.S. Pat. No. 3,793,158 to Hamilton discloses an amperometric type sensor for measuring relative concentration changes in gas stream components. The sensor is a galvanic device containing a liquid electrolyte and two identical electrodes. A reference chamber is connected to a sensing chamber and the cell is allowed to generate small amounts of current and the resulting cell voltage is measured. This system is deficient because the structure is susceptible to electrolyte leakage.

The measured changes in the resistance of the solid element is proportional to the concentration of gas in contact with the element. In each of the several examples of specific conductometric prior art gas sensing elements or cells discussed below, the systems are deficient because of high power usage and their resulting inability to operate for a long enough period of time under battery power.

U.S. Pat. No. 4,916,935 to Novack et al. describes a conductometric, solid state gas sensor with a linear output that incorporates a metal oxide semiconductor that is heated to yield an output proportional to gas contaminant.

U.S. Pat. No. 4,369,647 to Kitajima et al. describes a conductometric, gas leakage detector having a sintered metallic oxide block that changes thermal conductivity by chemical adsorption.

U.S. Pat. No. 3,864,628 to Klass et al. describes a conductometric, solid state gas sensor which is similar to a thermal conductivity gas sensor. A membrane of polyester is provided to give selectivity for hydrogen sensing, and polychloroprene is used for selective methane sensing.

For potentiometric sensors, the measured quantity is the potential of the sensing or indicator electrode versus a reference electrode. Potentiometric methods involve measuring the potential between reference and indicator electrodes at near zero current in the cell. The measurement is frequently performed under Nernstian conditions: for each decade change in gas concentration, a slope of approximately 60 mV/n is anticipated (at room temperature). The usual electron stoichiometry ('n') is typically 1 or 2. The assumption of a Nerstian response also implies a rapid equilibrium between the (sensing) electrode and the gas analyte. In many potentiometric gas sensors the active component is a pH electrode monitoring the pH of a solution in contact with an acid or basic gas (for example carbon dioxide or ammonia). The pH configuration is not the only embodiment. Other ion selective electrodes may be used, e.g. a silver sulfide electrode for hydrogen sulfide. Similarly, but more rare is the case of directly measuring the potential between two electrode elements (a reference element and a sensing element) and showing a voltage response proportional to the level of gas contamination. Potentiometric devices are noted for very low current drains; in fact, one needs as low a current as possible in order to make a valid measurement. Several examples of specific potentiometric prior art gas sensing elements or cells and their deficiencies are next discussed.

U.S. Pat. No. 5,302,274 to Tomantschger et al. discloses a specific potentiometric device. This device is based on three zones or compartments, i.e. central ion-conductive space wedged between a catalytic and reference space. The reference electrode employs an isolated "scrubbed" airspace to create a stable reference half-cell. A special housing is required to isolate the reference from contaminating gases and the housing is susceptible to electrolyte leakage.

U.S. Pat. No. 3,880,722 to Beltzer discloses a potentiometric carbon monoxide (CO) detector wherein the CO is first chemically oxidized (in solution) to form $CO_2$. The newly formed $CO_2$ shifts the pH of a solution, and this pH change is measured using a standard potentiometric pH electrode. Because special means are needed to enclose the electrolyte, this system is deficient since other non-toxic gases can also unintentionally shift the pH, and these devices generally respond too slowly to be an effective warning device.

Another problem which must be overcome by a successful gas sensor is the selectivity for an analyte (or analytes) in a matrix containing potential interferences. While some designs incorporate a transducer element selective to only the analyte of interest, others incorporate an outer membrane in order to impart some additional selectivity. These membranes rely on pores that allow the smaller analyte to pass while restricting larger-sized interferences. Other membrane strategies include solid membranes whereby the analyte is selectively soluble (extracted) in the membrane phase. All of these types of membranes are called "permselective" membranes. Permselective, as used herein, is intended to mean the selective permeation of one species over another through a barrier layer, which will include, for example, selectivity based on differences in molecular size, solubility in the barrier, ionic charge, or by other means. However, both these solutions work only with gross differences in molecular size or polarity. For many situations, such as for detection of small gas analytes amongst similarly-sized interferences, such a membrane is not selective enough.

One example of the need for selecting a specific analyte is in carbon monoxide sensors, especially those intended for home use. In order to meet current UL code, a home sensor should sound an alarm in an environment containing between 50 ppm to 400 ppm CO while remaining inactivated in an environment containing up to 500 ppm methane, 300 ppm butane, 500 ppm heptane, 200 ppm ethyl acetate, 200 ppm of isopropyl alcohol, or 1000 ppm of carbon dioxide. Since isopropyl alcohol (IPA) is easily oxidized, most CO detectors are acutely sensitive to vapors of this alcohol.

One strategy to avoid such false positives in an environment containing IPA is to use an absorber such as activated charcoal in front of the sensor. The charcoal has some affinity for the alcohol while being inert to CO. The difficulty with this approach is that eventually, under normal use, the capacity of the charcoal will be exceeded and some means of regenerating the absorber must be provided.

OBJECTS AND SUMMARY OF THE INVENTION

It is an object of the present invention to provide an electrochemical gas sensor to obviate the problems and limitations of the prior art systems.

It is a further object of the present invention to provide an improved electrochemical gas sensor which is sensitive to low concentrations of gas contaminants in the atmosphere being tested.

An object of the present invention is to provide an improved electrochemical gas sensor which is free of a liquid electrolyte, is less bulky, more readily miniaturized, and in which both the sensor and reference electrodes can be exposed to the atmosphere being monitored.

Yet another object of the present invention is to provide an improved electrochemical gas sensor which is sensitive to low concentrations of carbon monoxide.

Still another object of the present invention is to provide an improved electrochemical gas sensor which is inexpensive to manufacture and has a long operational lifetime.

Another object of the present invention is to provide a gas sensor with a selective filter or layer which selectively allows only gas molecules of interest to contact the sensor electrode.

A further object of the present invention is to construct a selective filter or layer from membranes that are microporous, nanoporous, permselective, adsorptive and/or chemically reactive which only allow small gas molecules of interest, such as carbon monoxide, to pass therethrough, while restricting, rejecting, removing, or chemically reacting with interfering gas molecules.

Still, a further object of the present invention is to provide a multichannel gas sensor device for monitoring more than one toxic/flammable gas.

A further object of this invention is to provide a multifunctional or multilayer gas sensor capable of sensing environmental variables including humidity, temperature, pressure, and other internal references as needed, i.e., for other gases, to selectively and automatically compensate for changes in the environmental variables.

In accordance with the invention, there is provided an electrochemical gas sensor that has a catalytically active sensor electrode and a reference electrode which can both be exposed to the atmosphere being monitored. The sensor electrode is separated from the reference electrode by an ion conducting substrate. The nature of the electrodes, and the manner in which they are mounted to the substrate is discussed hereafter. While it is important that the sensor electrode be sufficiently sensitive to low concentrations of gas contaminants in the atmosphere being tested, the reference electrode can also be exposed to the contaminants in the atmosphere.

Among the gases that may be tested for are gases and volatile substances as diverse as carbon monoxide; carbon dioxide; oxides of nitrogen; oxides of sulfur; hydrides of nitrogen such as ammonia, primary and secondary amines and hydrazine; hydrides of phosphorus such as phosphine, sulfur such as hydrogen sulfide, arsenic or boron; silicone such as silanes; halogens such as chlorine; mercaptans; aldehydes; hydrogen; unsaturated and saturated hydrocarbon vapors; halocarbons; and alcohols such as methanol and ethanol. A specific sensor can be devised using suitable sensor and reference electrodes to test for any toxic, combustible or flammable gas, or generally volatile substances which may be oxidizable. The enclosed volumes within which such gas contaminant monitoring may take place include those suggested above, as well as ordinary residential housing, parking garages of all sorts, vehicles, interiors of commercial or industrial buildings, hospitals, and mines.

Further, in accordance with the invention, a filter element constructed of an immobilized chemical element, a solid membrane, or a porous membrane is used in conjunction with an electrochemical gas sensor which only allows selective gas molecules to pass through to the sensor electrode of the gas sensor.

According to one embodiment of the invention, a gas sensor for detecting the presence of a gas contaminant in a gas sample being monitored has a first electrically conductive electrode which interacts with the gas contaminant present in the gas sample and a second electrically conductive electrode which does not interact with the gas contaminant present in the gas sample. The first and second electrically conductive electrodes are mounted to an ionically conductive substrate. A potentiometric voltage measuring circuit is connected to the first and second electrically conductive elements. A filter layer through which the gas being sampled flows prior to being exposed to the first and second electrically conductive electrodes can be incorporated into the design.

In accordance with the invention, a method for sensing the presence of a gas contaminant in a gas sample being monitored comprises the following steps. An ionically conductive substrate having first and second electrically conductive electrodes mounted on opposite sides thereof is exposed to the gas sample. A first voltage signal originating in the difference between the first and second electrically conductive electrodes, respectively, is generated. The first voltage signal is compared with a predetermined reference voltage signal and a trigger signal indicating the presence of the contaminant gas is generated whenever the first voltage signal is less than the reference voltage signal. An alarm can be actuated with the trigger signal. In some applications, interference gases are removed from the gas sample prior to exposing the electrically conductive electrodes with the gas sample.

Also, according to another embodiment of the invention, there can be a multiple layer potentiometric sensor device for detecting the presence of one or more gas contaminants in a gas sample being monitored. The sensor device has a casing with top and bottom sections and openings through the top section. A filter layer is disposed in the interior of the casing for dividing the interior into first and second chambers wherein the first chamber includes the top section of the casing and the second chamber includes the bottom section of the casing. An ionically conductive substrate is disposed in the second chamber and has at least one gas sensing electrode mounted to an upper surface thereof. A reference electrode is mounted to a lower surface of the ionically conductive substrate. At least one environmental variable sensing electrode is mounted to the upper surface of the second ionically conductive substrate. However, the performance of this sensor is unaffected by gases communicating across both chambers.

The embodiment described immediately before has a novel method for detecting the presence of one or more gas contaminants in a gas sample being monitored. First, the gas sample is passed across a filter layer disposed in the interior of a casing to remove any interference gas from the gas sample. Then, an ionically conductive substrate having at least one gas sensing electrode and at least one environmental variable sensing electrode mounted to one surface thereof and a reference electrode mounted to a different surface thereof are exposed to the gas sample subsequent to the removal of the interference gas. Voltage differences are measured between the reference electrode and the gas sensing electrode ($V_1$), or the environmental variable sensing electrode and the reference electrode ($V_2$). Changes in at least one environmental variable are compensated for by subtracting a function of the voltage generated at the environmental variable sensing electrode from the first voltage generated at the gas sensing electrode. This third compensated voltage signal ($V_3$) is compared to a predetermined threshold value. A trigger signal is generated indicating the presence of the contaminant gas whenever the third voltage signal is less than the reference signal. The environmental variable sensing electrode cannot produce a significant signal upon exposure to the contaminant of interest.

BRIEF DESCRIPTION OF THE DRAWINGS

The structure, operation, and advantages of the presently preferred embodiment of the invention will become further apparent upon consideration of the following description taken in conjunction with the accompanying drawings, wherein.

DETAILED DESCRIPTION OF THE INVENTION

Figure 1:
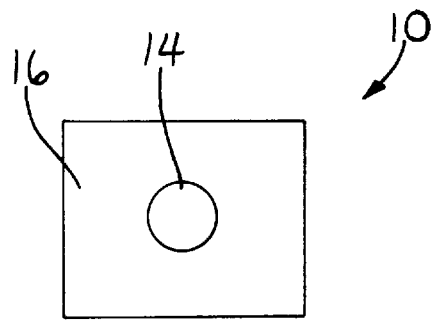
FIG. 1 is a schematic illustration of a top, plan view of a first embodiment of a solid state sensor having a sandwiched construction, in accordance with the invention.
Figure 2:
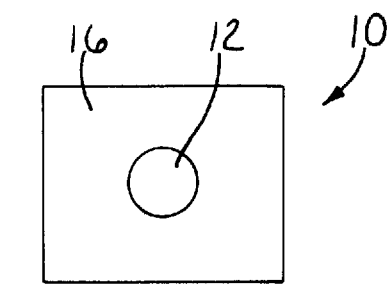
FIG. 2 is a schematic illustration of a bottom, plan view of the first embodiment of a solid state sensor shown in FIG. 1.

Referring to FIGS. 1 and 2, there is illustrated a first embodiment of a solid state, potentiometric, gas sensor 10 incorporating a sensing or catalytic electrode 12 and a reference electrode 14. The catalytic and reference electrodes 12 and 14, respectively, are formed of dissimilar electrically conducting materials and are connected by an ionically conductive element or substrate 16. A potential can be generated between the electrodes 12 and 14 when sensor 10 is subjected to a gas sample containing contaminant gases, such as for example, CO, hydrazine, $H_2S$, hydrocarbons, and alcohols. A key aspect of the invention is that only the catalytic electrode 12 responds to the contaminant gas in the gas sample while the reference electrode 14 remains inert and substantially unresponsive. Thus, both the catalytic and the reference electrodes 12 and 14, respectively, of the gas sensor 10 can be exposed to a gas sample containing a contaminant gas and there is no longer the need to isolate the reference electrode 14 from the contaminant gas, as typically required by the prior art sensors described herein before. Also, the gas sensor 10 of the present invention operates in a temperature range of about −40° F. to about 200° F. Furthermore, since a solid, ion-conducting substrate 16 is employed, there is no need for inert plastic, liquid phase separators, or encapsulation of the liquid phase as was typically the case in the prior art sensors described herein before.

Preferably, the sensing or catalytic electrode 12 is comprised of nobel metal catalysts such as platinum, palladium, rhenium, ruthenium, gold, silver, and mixtures or alloys thereof; carbon blacks and carbon fibers; pure metal or metal coated structures, metal such as carbon, metal fibers, or metallic particulate deposited onto support structures; polypyrrole; tungsten, titanium and oxides thereof; organometallic compounds containing elements from the group consisting of cobalt, iron, and nickel; and transition metal complexes containing elements from the Periodic Table of Elements Groups IIIA, IVA, VA, VIA, VIIA, VIIIA, IB, IIB or other metals responsive to a contaminant gas, such as carbon monoxide, $H_2$, $N_2H_4$, $H_2S$, $PH_3$, arsine, alcohols (methanol, ethanol, propanol, iso-propanol, etc.), as well as other toxic, combustible or hazardous vapors. These electrode materials could be constructed into a gas diffusion type electrode structure such as those described for use in fuel cells, as described in the product catalog of E-Tek, Inc. of Natick, Mass. The catalytic electrode 12 can also be constructed as a membrane electrode assembly by depositing metal and ion-conductive electrolyte onto a layer of material selected from the group comprising an ion-conducting polymer, an ion-conducting organic polymer, an ion-conductive solid state electrolyte, and a layer of fiber assemblies. Depending on the property desired, it is not essential to mix the metal or carbon with an ion-conductive electrolyte. The solid state electrolyte can be selected, for example, from commercially available Nafion®, Neosepta®, and Raipore® membranes. The fiber assemblies consist of the catalytic element itself or the catalytic element affixed to a fiber assembly consisting of carbon fibers, carbon black, carbon particulates, metallic fibers, metallic particulates or mixtures thereof coated with a material from the group consisting essentially of platinum, platinum black, palladium, iridium, ruthenium, tungsten, gold, cobalt selenite, platinum/palladium alloy, palladium/rhodium alloy, gold/ruthenium alloy, or organometallic compounds containing elements from the group consisting of cobalt, iron, nickel, or transition metal complexes containing elements from the Periodic Table of elements, groups IIIA, IVA, VA, IIIA, VIIA, VIIIA, IB, IIB. The catalytic electrode 12 can be pressed into the ion-conducting substrate 16, or deposited as a metal from a salt directly onto or into the ion-conducting substrate 16, as discussed in more detail below.

The reference electrode 14 can be a layer of material constructed of any stable, reliable, non-interfering redox couple such as any metal/metal halides or metal ions, for example, silver/silver ion, silver/silver chloride, silver/silver halide, mercury/mercury chloride, or mercury/mercury halide; stable metal oxides; metal compounds, or carbons not responsive to the contaminant but capable of forming a stable electrode potential; organic redox couples; organometallic redox couples; transition metal complexes; and pH electrodes. The reference electrode 14 can be in the same form as detailed for the catalytic electrode example above. That is, the reference electrode layer can be constructed of a coated metal, such as silver deposited on a layer of carbon, electronically conductive polymer, or a layer of fiber assemblies consisting of the silver itself or the silver affixed to a fiber assembly consisting of both carbon and metallic fibrous elements. The reference electrode 14 can be pressed into the ion-conducting substrate 16, or deposited as a metal from a salt directly onto or into the ion-conducting substrate 16, as discussed in more detail below. In addition, the reference electrode 14 can be constructed of a wire, plate, or solid foil of the electrode material pressed into the ion conducting substrate 16. Furthermore, a conductive metal epoxy, such as silver epoxy could be applied directly to the ion conducting substrate 16.

The ion-conductive element 16 can be an ion-exchange membrane constructed of such materials such as Nafion® available from the Dupont Corporation of Delaware, Neosepta® from the Tokuyama Soda Corporation of Japan, suitable Raipore® ion exchange membranes from the Pall RAI, Inc. of Hauppauge, N.Y., or ion-conducting polymers such as doped polyvinylchloride, polyphenyleneoxide, polyphenyleneglycol, polythiophenes, polypyrrols, polydibenzocrown ethers, polyphenylenes, substituted polyacetylenes, some specially doped ceramic material or combinations of these polymers. The ion-conductive substrate 16, if of the ion-conductive organic polymer type, can comprise acid functionality such as —$SO_3H$, —$CO_2H$, —$PO_3H$; totally or partially neutralized acid functionalities such as —$CO_2Na$, —$SO_3K$, along with none or some of the free acid functionality, respectively, etc.; amine functionalities such as —$NR_1R_2$ where $R_1$ and $R_2$ are H, alkyl, aryl, heterocyclic (like polyvinylpyridine), etc.; totally or partially neutralized amine functionalities such as —$NR_1R_2$—HX where X is halide (such as $Br^-$, $Cl^-$, $F^-$); $HSO_4^-$; $HPO^{2-}_4$; carboxylic acid (such as acetate, propionate, benzoate);

quaternary ammonium functionalities (such as $R_4N^+X^-$); ionically doped polymers; and doped ceramic material.

The catalytic and reference electrodes 12 and 14, respectively, as shown in FIGS. 1 and 2, are affixed to opposite sides of the ion-conducting substrate 16 to insure intimate contact between the electronically conducting electrodes and the ion-conducting substrate. The method of attaching the electrodes 12 and 14 to substrate 16 is not critical to the invention and can be carried out via mechanical contact, pressure bonding, heat bonding, ultrasound welding, heat sintering, solvent bonding, inert polymer "gluing", or making the electrodes an integral part of the substrate by depositing metal electrodes into or onto substrate 16. Combinations of the attaching methods can be used with limitations depending on the stability of the ion-conducting substrate 16, the sensor performance, i.e., the ability to output a response of typically at least 0.5 mV/ppm of CO.

Figure 3:
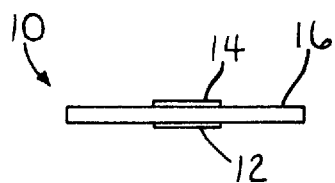
FIG. 3 is a side view of the solid state sensor shown in FIGS. 1 and 2.
Figure 4:
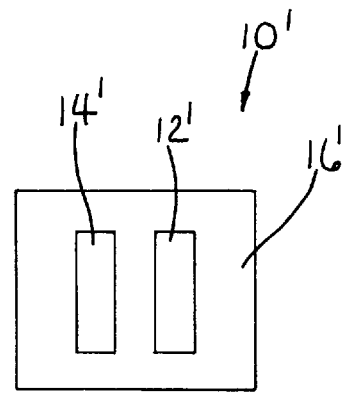
FIG. 4 is a schematic illustration of a plan view of a second embodiment of a solid state sensor having a side-by-side assembly, in accordance with the invention.
Figure 5:
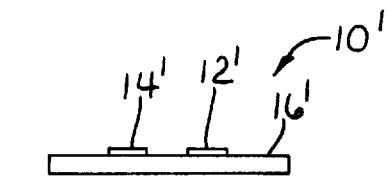
FIG. 5 is a side view of the solid state sensor shown in FIG. 4.

There are two preferred means of assembling electrodes 12 and 14. As shown in FIGS. 1, 2, and 3, the first embodiment of sensor 10 has a sandwiched construction with the sensing electrode 12 on one side of substrate 16 and the reference electrode 14 disposed on the opposite side of substrate 16 from the sensing electrode. In a second embodiment, as shown in FIGS. 4 and 5, sensor 10' is constructed in a side by side arrangement with both sensing electrode 12' and the reference electrode 14' disposed on the same side of substrate 16' in spaced relationship to each other. Throughout the specification, primed and double primed numbers represent structural elements which are substantially identical to structural elements represented by the same unprimed number.

An example of a gas sensor 10, in accordance with the first embodiment as shown in FIG. 1, has an ion-conducting substrate 16, constructed from a Nafion® 117 membrane available from E. I. DuPont Corp. of Wilmington, Del., a catalytic electrode 12 formed from a composite of carbon and nickel fibers with catalytic platinum deposited on the fibers, and a reference electrode 14 constructed of carbon and nickel fibers. The sensor 10 is assembled with substrate 16 sandwiched between catalytic electrode 12 and reference electrode 14. Then the sensor assembly 10 is heated to fuse the two electrodes 12,14 and the substrate element 16 together.

Figure 6:
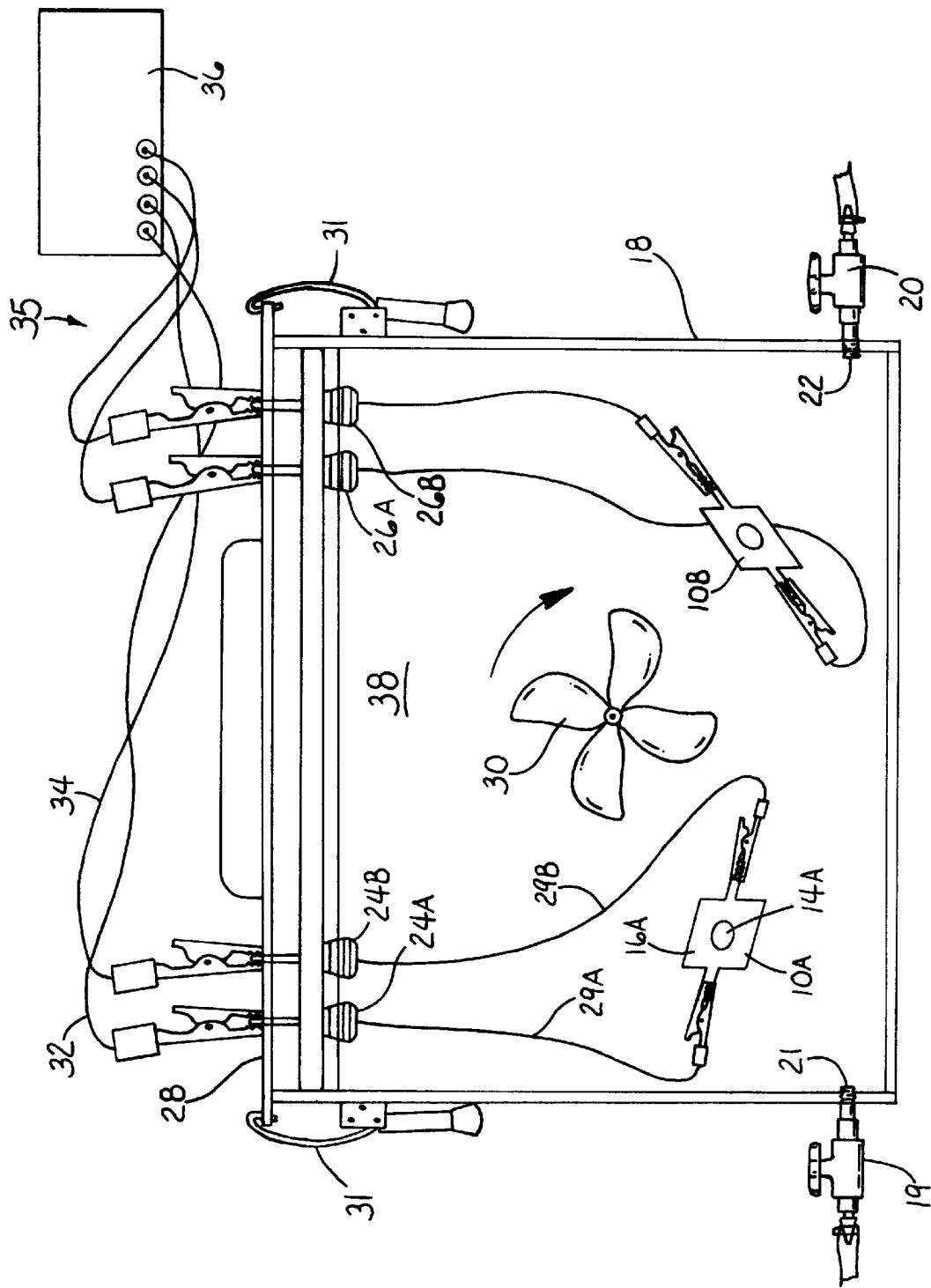
FIG. 6 is a schematic illustration of a Figaro test box modified to concurrently test two solid state sensors.

A number of tests, discussed below, were conducted by placing one or more of the gas sensors 10A, 10B in a plexiglas Figaro test box 18 manufactured by Figaro Corp., of Wilmette, Ill. Gas sensors 10A and 10B can be selected from either the first or second embodiments of gas sensors 10 and 10', respectively. For the purpose of experimentation, sensor 10 was used and described herein. The test box 18, as shown in FIG. 6, has a volume of 5 liters (L), has valved inlet and outlet conduits 19, 20, respectively, mounted to gas inlet and gas outlet openings 21,22, respectively. Electrical connectors 24A,24B,26A,26B, secured to a removable lid 28 of box 18. The test box 18 is arranged with clamps 31 to secure the lid 28 to the base of the box 18 with a nearly gas tight seal. An electrical fan 30 is mounted within box 18 to ensure gas mixing.

To conduct one test (not illustrated), a gas sensor 10 was placed in a test setup incorporating a box 18, of the type shown in FIG. 6 and the catalytic electrode 12 and reference electrode 14 of the gas sensor 10 were electrically connected by wires 29A,29B to electrical connectors 24A,24B in lid 28. Then, box 18 was sealed with the clamped lid 28. The electrical connectors 24A,24B were then connected by wires 32 and 34, respectively, to a National Instruments interface card mounted within a conventional PC computer 36. An important aspect of the invention is that no additional modification of the gas sensor 10 is necessary. That is, both the catalytic and reference electrodes 12 and 14, respectively, are exposed to the same gases within chamber 38 of box 18.

The method for sensing the presence of a gas contaminant in a gas sample being monitored typically comprises the following steps. First, the ionically conductive substrate 16 having the sensor and reference electrodes 12 and 14, respectively, mounted thereto is exposed to a gas sample. The voltage output from the sensor and reference electrodes 12 and 14, respectively, is directed through a circuit which compares a first voltage signal, corresponding to the difference between the voltage signals output by the sensor and reference electrodes 12 and 14 with a reference voltage signal. A trigger signal is generated indicating the presence of the contaminant gas whenever the first voltage signal is less than the reference voltage. Alternatively, the voltage output from the sensor and reference electrodes 12 and 14 can be changed to a first digital input and operated on by a computer 36 which compares the difference in the first digital inputs with a reference digital input. A trigger signal is generated by the computer indicating the presence of the contaminant gas whenever the difference in the first digital input is less than that of the reference digital input. The computer can then output the trigger signal to show the results on a monitor, a meter, and/or to activate an alarm device.

During the testing of a gas sample with gas sensor 10, the electrodes 12 and 14 output voltage signals to a potentiometric, voltage measuring circuit 35. The measuring circuit 35 can include computer 36, a monitor, and an alarm device, as desired. In the test setup of FIG. 6, the potential difference from the electrodes 12 and 14 are recorded in computer 36 using a data acquisition program that records voltages on up to eight channels. For example, the data acquisition package could be custom software using LabView for Windows programming language, available from National Instruments of Austin, Tex. Similarly, electronic circuitry from a common smoke detector could be adapted to perform a similar task. Open circuit potentials across electrodes 12 and 14 are monitored periodically (for example 30–300 seconds) and written to a storage disk within conventional computer 36. While a computer is shown, it is also within the terms of the invention to incorporate a voltmeter or other similar electrical measuring device in voltage measuring circuit 35 in place of or in conjunction with computer 36. Also, the simplicity of the sensor design does not necessitate the use of a PC. Common micro computer circuitry found in consumer devices such as smoke alarms or washing machines can be used effectively.

Figure 7:
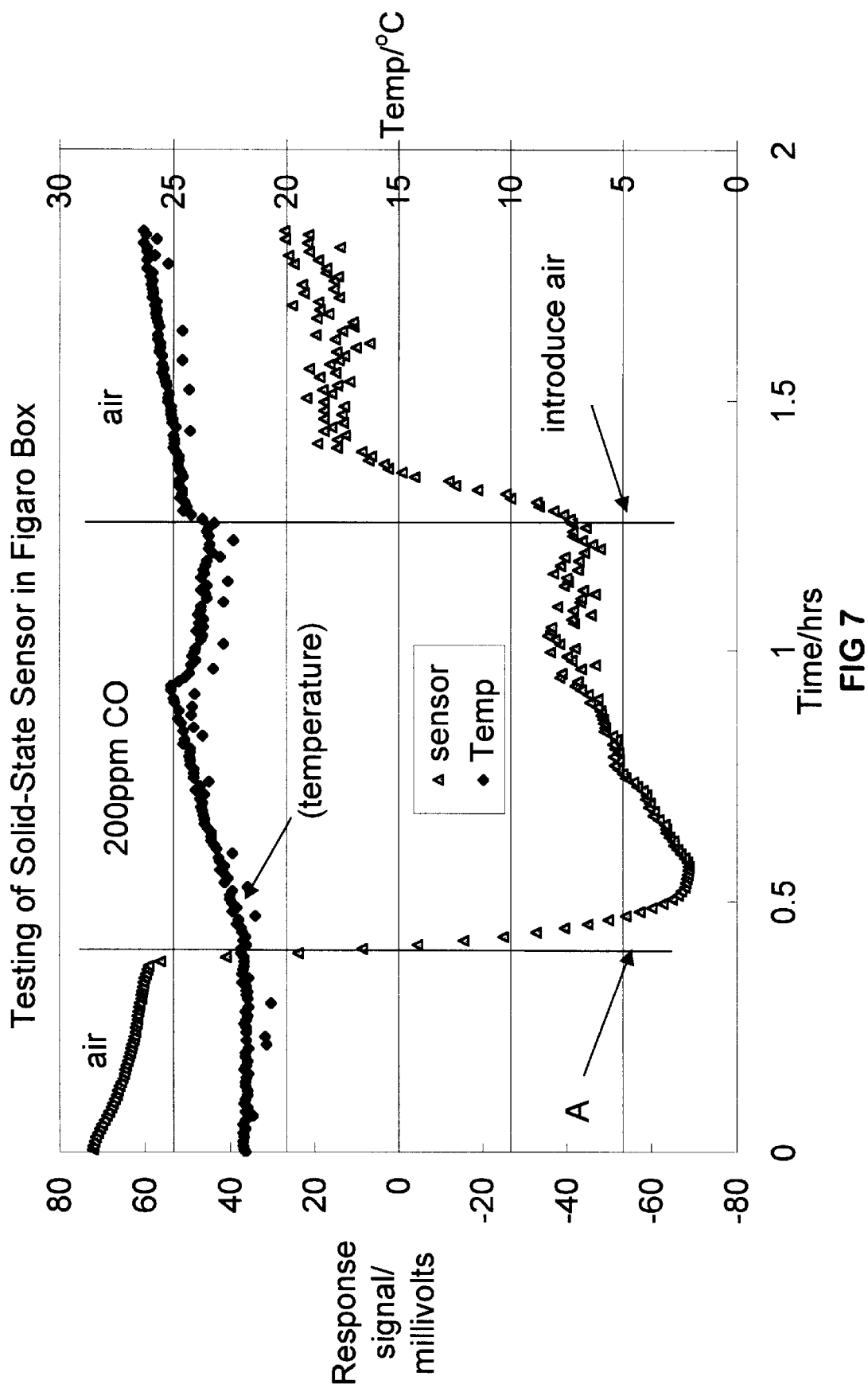
FIG. 7 is a graph showing the test results of exposing a solid state sensor of the present invention (the sensor having a side-by-side configuration) to a sample gas containing CO.

FIG. 7 is a graph showing the test results from the exposure of gas sensor 10' in chamber 38 of Figaro Box 18 to air and 200 parts per million (ppm) CO at a temperature of about 22.5° centigrade (C.) to about 25° C. Using a test setup, similar to that shown in FIG. 6, a single side-by-side sensor 10' with a catalytic platinum electrode 12', a carbon reference electrode 14 and a Nafion® 117 substrate 16 was first subjected to a sample of air and then to air contaminated with 200 ppm of CO. To conduct the test, chamber 38 was first flooded with air during the first 0.4 hrs of the test. Then, contaminated air with 200 ppm of carbon monoxide was injected through gas inlet 19. The graph of FIG. 7 traces a rapid and reversible response to carbon monoxide. The response signal along the vertical line at 0.4 hr. drops from about +60 millivolts (mv) to −70 mv at 0.5 hr. due to the 200 ppm of CO introduced into the box 18 between 0.4 and 1.25 hrs. The output of sensor 10 responded to the presence of CO by dropping significantly to the range of about −70 mv to about −40 mv. Then, when the contaminated air was replaced with an air sample free of the CO at 1.25 hrs., the response signal rapidly increases and approaches the baseline. The results of the test shown in the graph of FIG. 7 show that a gas sensor 10 can output a reference signal indicating the presence of a contaminant in a gas sample. This test also shows that both the catalytic and the reference electrodes 12' and 14', respectively, of the gas sensor 10' can both be exposed to a gas sample containing a contaminant gas being monitored and still output a reliable reference signal indicating the presence of a contaminant. Thus, one feature of the sensor 10' is that there is no need to isolate the reference electrode from the contaminant gas, as with prior art sensors described before.

Figure 8:
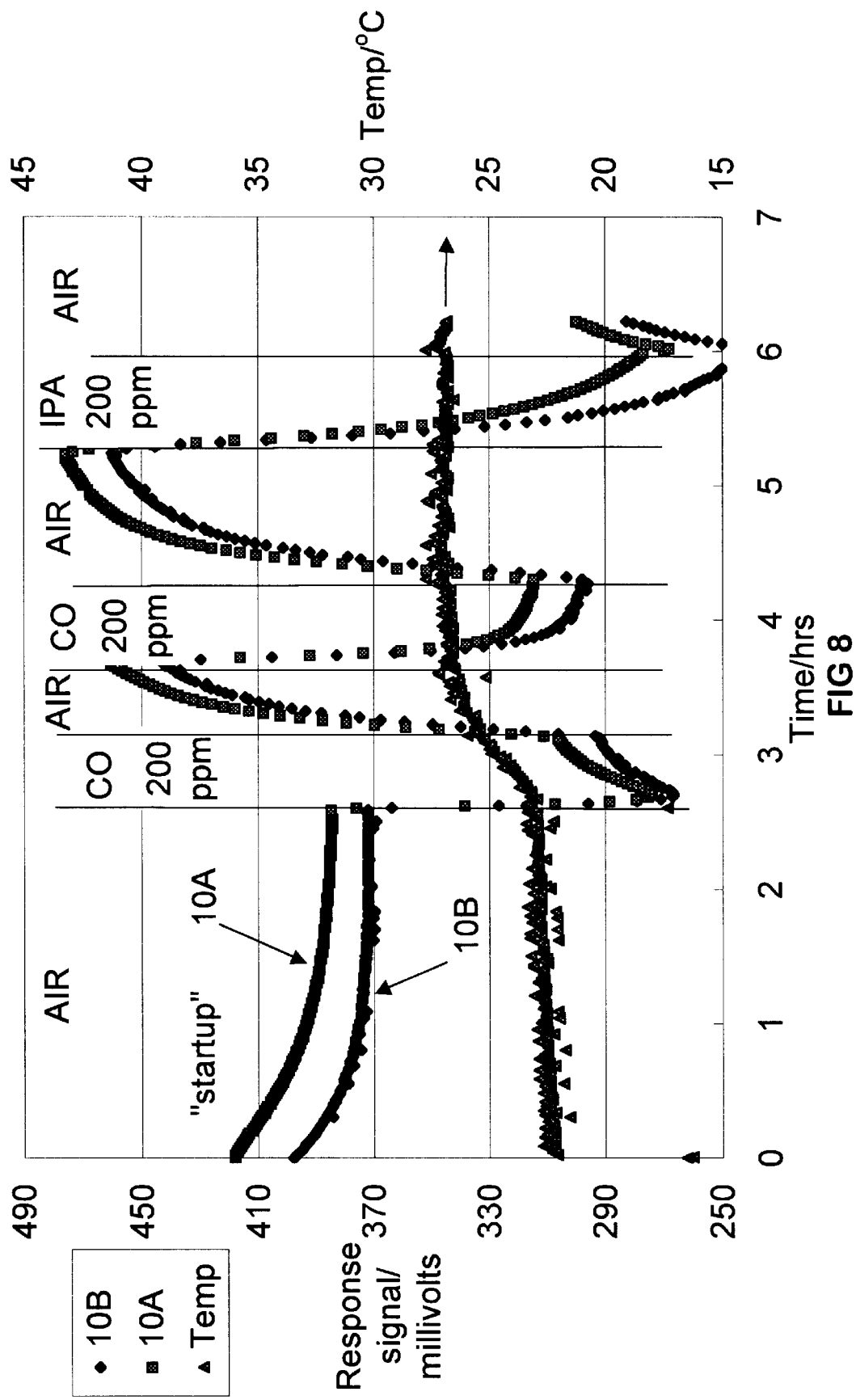
FIG. 8 is a graph showing the test results from exposing two identical solid state sensors of the present invention (the sensor having a sandwich configuration) to a sample gas containing CO.

The results of a second test, as shown in the graph of FIG. 8, are for two identical gas sensor assemblies 10A,10B of a sandwiched construction with a catalytic electrode 12A of platinum on carbon black and a reference electrode 14A of silver on carbon black sandwiched about a substrate 16A of Nafion® 117. The silver and platinum loading for both electrodes 10A,10B is a 10% by weight loading of metal on Vulcan X-72 carbon black. Both of the electrodes were about 1.0 cm in diameter. The two gas sensor assemblies 10A, 10B are electrically connected within a Figaro test box 18, as shown in FIG. 6.

FIG. 8 shows the response of the two identical sensor assemblies 10A, 10B in Figaro box 18 to cycles of air and air with 200 ppm CO. During startup, from 0 to 2.5 hours, sensors 10A and 10B output a response signal of between about 420 mv and about 370 mv. Then, during the next period of about 0.6 hours, when the chamber 38 of box 18 is flooded with air containing 200 ppm of CO, there is a fast response by the sensors and the trace of the response signal drops to between 270 mv and 280 mv. Then for the next 0.5 hrs, chamber 38 is again flooded with air and the sensors 10A and 10B immediately respond as indicated by the rapid increase in the trace of the response signal to about 440 mv to 460 mv. Continuing with the test, chamber 38 of box 18 is again flooded with air containing 200 ppm of CO for about 0.75 hours and there is a fast response by the sensors as indicated by the trace of the response signal dropping to between 300 mv and 310 mv. Finally, chamber 38 of box 18 is flooded again with air and the signal output of sensor assemblies 10A, 10B increases to a level which indicates the absence of CO in the air. The differences in the baselines of sensors 10A and 10B is caused by a difference in the starting and ending temperature and/or relative humidity in the box 18. Heat is generated by the operation of fan 30, and there is a difference between the ambient relative humidity and that in the make-up gases introduced into the box.

In a third test, a different sensor assembly 10' is constructed with a ion-conducting substrate 16' formed of a Nafion® 117 membrane, a catalyst electrode 12' formed of a composite of carbon and nickel fibers with a platinum catalyst deposited on the carbon fibers, and a reference electrode 14' of carbon and nickel fibers free of the platinum catalyst. The electrodes 12' and 14' are fused onto the Nafion® substrate 16'. The sensor 10' of this test primarily differs from the sensor 10, used in the tests described above, in that here the configuration of reference and catalyst electrodes 12', 14', respectively, are side-by-side on the same side of the Nafion® substrate 16', as shown in FIG. 4. The sensor assembly 10' is formed with the sensor and reference electrodes 12', 14' being substantially rectangular in shape and placed adjacent to each at a spacing of approximately 2 mm apart.

Figure 9:
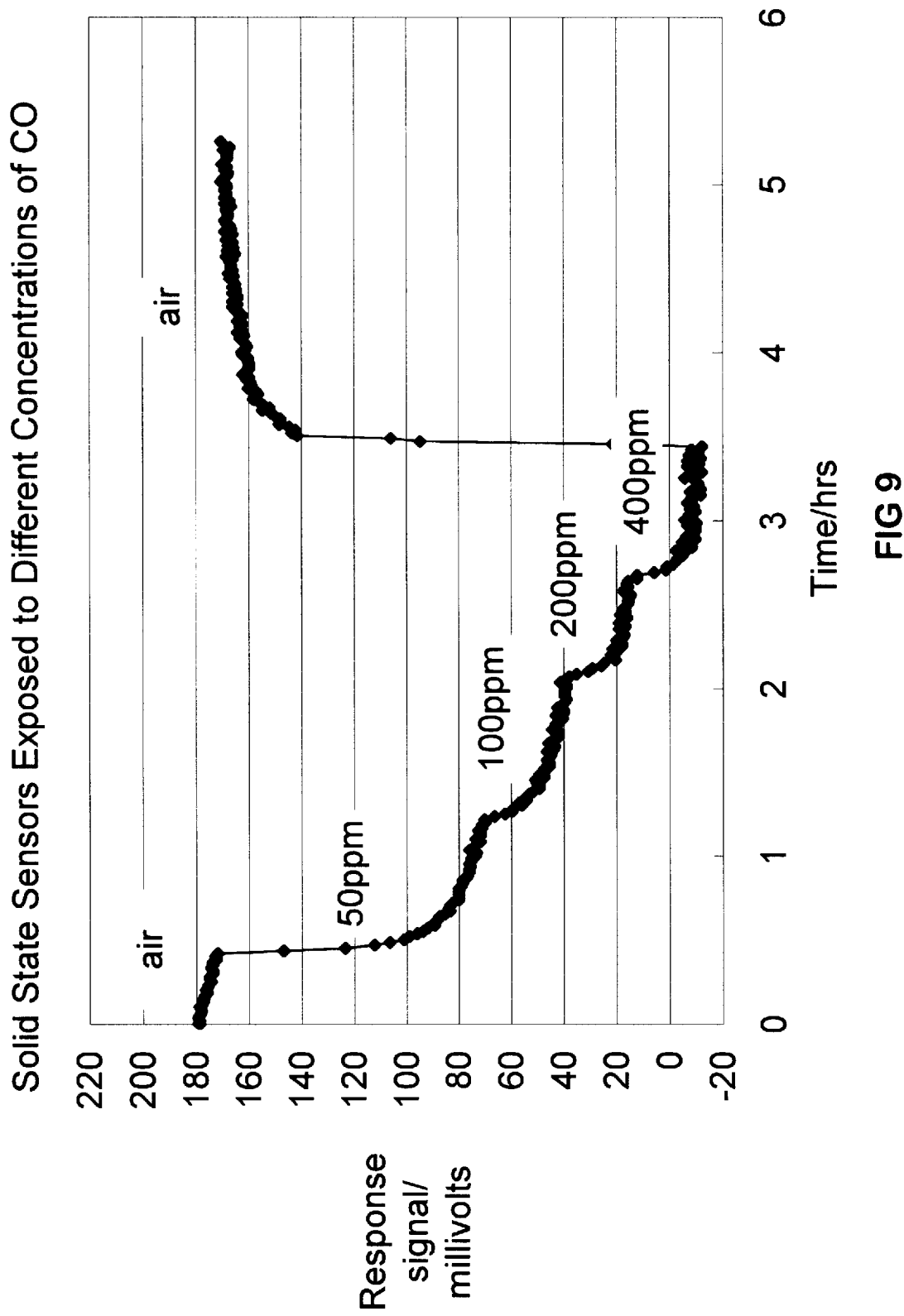
FIG. 9 is a graph showing the test results from exposing a solid state sensor of the present invention (the sensor having a side-by-side configuration) to a sample gas containing different amounts of CO.
Figure 10:
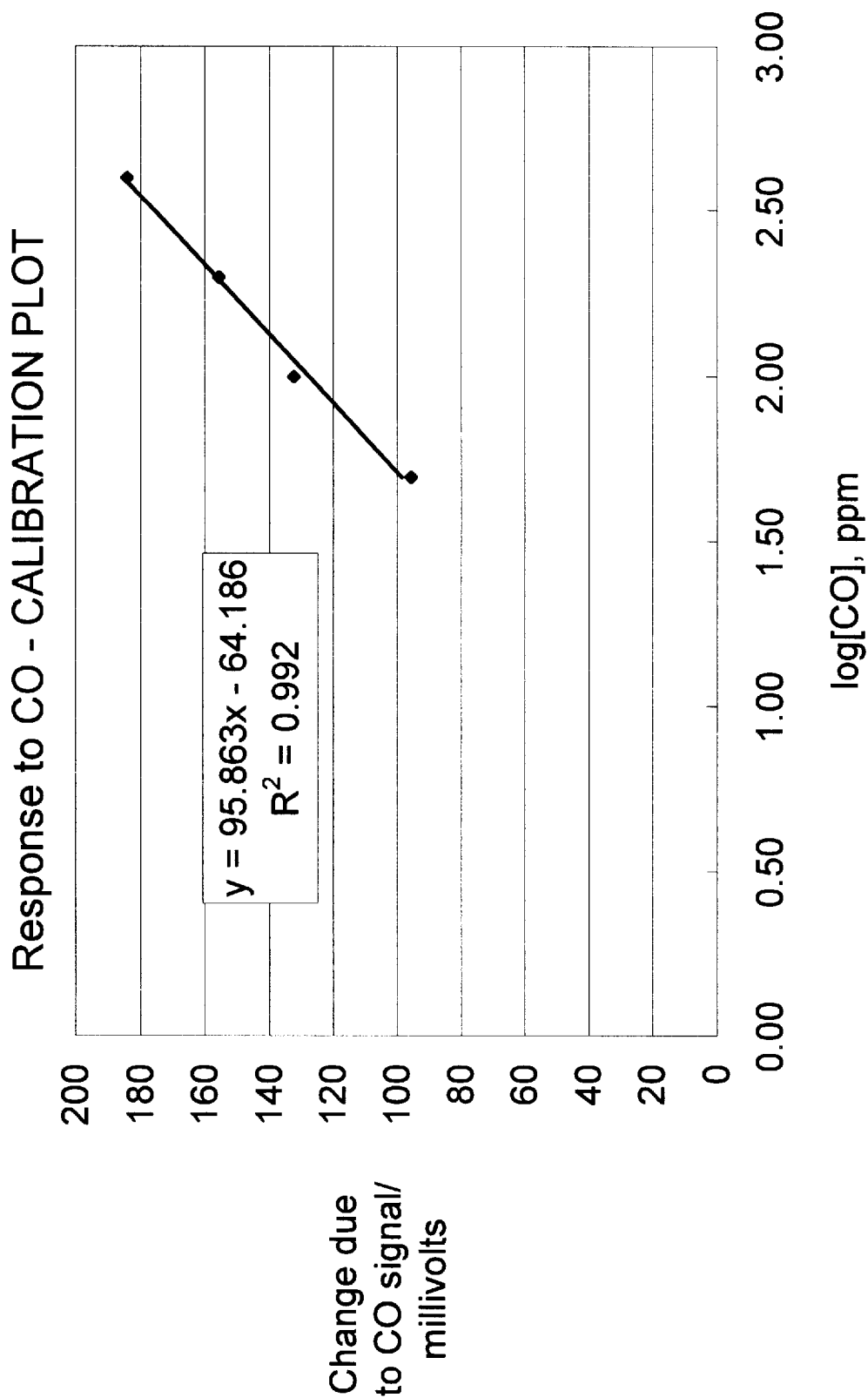
FIG. 10 is a calibration plot of the data from graph of FIG. 9.

As in the previously described tests, each of the electrodes 12' and 14' of sensor 10' is connected to lid 28 of a test setup incorporating a box 18, of the type shown in FIG. 6, and then connected to a National Instruments interface card in computer 36 incorporating a data acquisition package of custom software written via Lab View for Windows. Subsequent to placing the sensor 10' in the test box 18, the box is sealed with the clamped lid 28. No additional modification or holder is used with sensor 10'; that is both the sensor and reference electrodes 12', 14' are exposed to the chamber environment. Open circuit potentials were monitored every 30–60 seconds and written to disk. FIG. 9 shows the results of sensor assembly 10' exposed to air samples with successively greater concentrations of carbon monoxide. The trace shows that steady-state responses are obtained in approximately 10 minutes. FIG. 10 shows a linear response log of CO concentration in ppm versus the response signal in mV obtained over the range of CO concentrations employed. Using a linear response curve, the amount of carbon monoxide can be easily determined for a given response signal.

Both embodiments of the potentiometric gas sensors 10,10', described above, are advantageous because they use a solid substrate 16,16', respectively, at a temperature of about −40° F. to about 160° F. and do not require additional water or liquid electrolyte. The elimination of a liquid electrolyte dramatically simplifies the construction and operation of these sensors. Hard-to-control variables such as the wetting properties between the sensor electrode and the liquid electrolyte are eliminated. The cost of the sensors is reduced since the more complex gas diffusion electrodes are eliminated. The need and difficulty of isolating the reference electrode from the contaminated atmosphere is eliminated. Also, the sensor can incorporate catalytic and reference electrodes of different compositions which are both exposed to the contaminant gas.

The catalytic sensor 12 can be "dry", i.e., at ambient humidity levels; or it may be imbibed with high-boiling, low vapor pressure inert solvent, i.e., a polyether, such as polyethylene oxide or polyethylene glycol, or, it may be encapsulated and contain water, salt, acid, alkali, etc. The reference electrode 14 would be uncatalyzed in this case.

Figures 11, 12:
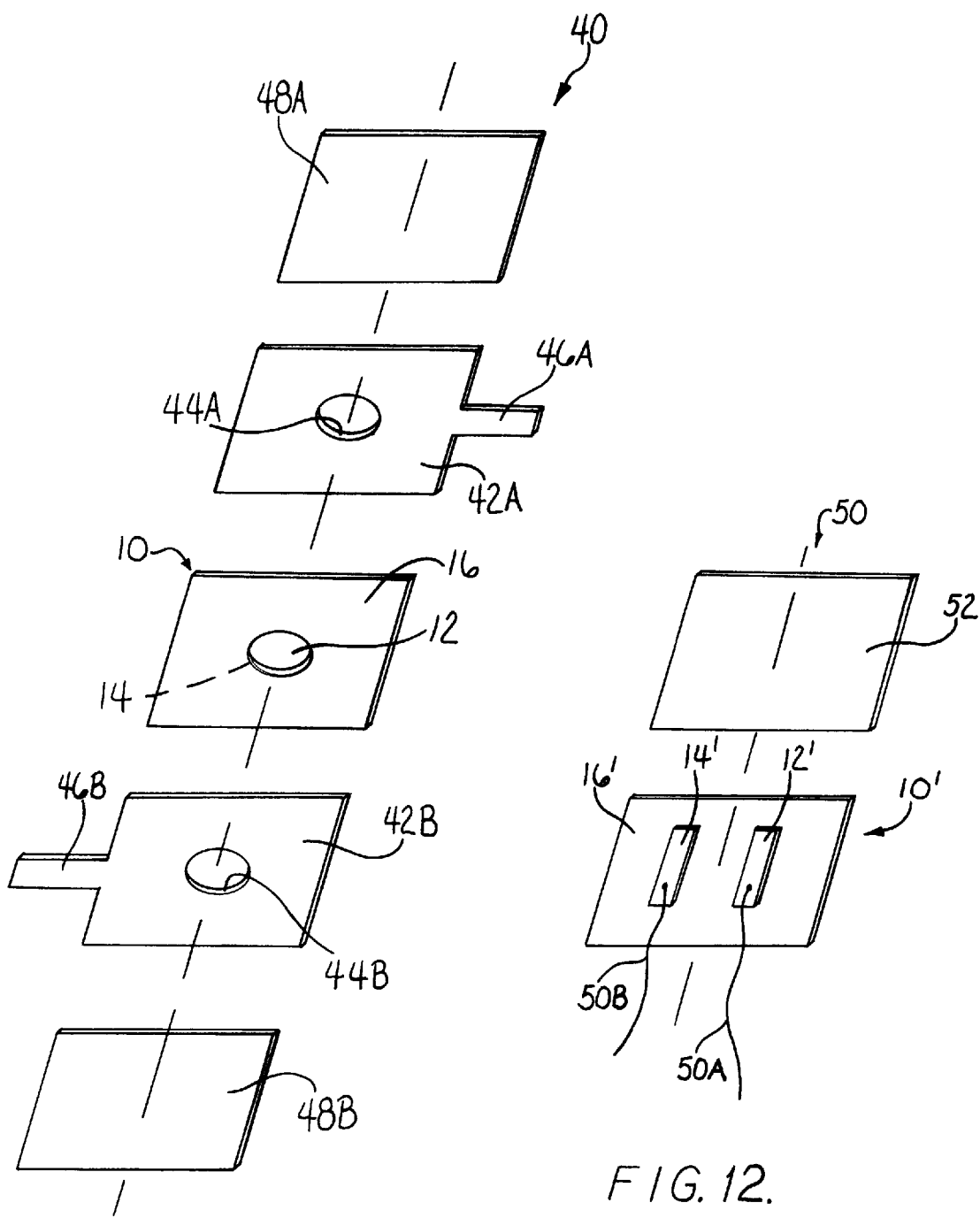
FIG. 11 is an exploded view of a sensor assembly including sensor and reference electrodes sandwiched about a substrate with current contacts and filter material on either side.
FIG. 12 is an exploded view of a side-by-side sensor assembly covered with a filter material.

FIG. 11 shows an exploded view of a sensor assembly 40 incorporating a sandwiched sensor 10. The sensor assembly 40 includes electrical contact members 42A,42B which are rectangularly shaped, electrically conductive sheets with apertures 44A,44B therethrough and electrical contacts 46A, 46B, respectively, extending outward from one side. The contact members 42A, 42B are preferably formed of carbon paper but can be of other conducting substances like nickel or silver mesh. The contact members 42A,42B are disposed in sandwiched relation about sensor 10 and are in electrical contact with the catalytic and reference electrodes 12, 14 while allowing a surrounding gas to contact the electrodes through the apertures 44A,44B.

Also, in accordance with the invention, sensor assembly 40 can be provided with two additional layers 48A, 48B of filter material (described herein) which are sandwiched about the outwardly facing sides of contact members 42A, 42B, respectively. The filter material (as described below) can be selected to absorb specified contaminant gases and to prevent the sensor from outputting a reference signal caused by the presence of the contaminant gas in the gas being monitored, i.e. to eliminate an output signal from the presence of isopropyl alcohol, a typical contaminant found in a residential environment. The sensor assembly 40 can be constructed in a package by attaching the catalytic and reference electrodes 12,14 to substrate 16, contact members 42A,42B to the substrate 16, and the filter layers 48A, 48B via pressure bonding, heat bonding, heat sintering, solvent bonding, or inert polymer "gluing" and combinations thereof to the contact members and/or to the substrate.

Referring to FIG. 12, there is illustrated an alternative sensor assembly 50 with contact wires 50A, 50B electrically connected to catalytic and reference electrodes 12' and 14' on a substrate 16' of sensor 10'. It is also within the terms of the invention to use an electrically conductive, contact member (not shown) with two holes aligned with the electrodes to replace wires 50A, 50B. An additional layer 52 of filter material, similar to the layers 48A, 48B of filter material described for the embodiment shown in FIG. 11, is attached to substrate 16' to cover the electrodes 12' and 14'. As discussed with regards to the embodiment illustrated in FIG. 10, the filter material is selected to absorb certain predetermined contaminants and eliminate the electrical signal caused by the presence of that contaminant, i.e. to eliminate a signal from isopropyl alcohol, a typical contaminant found in a residential environment.

Figure 13:
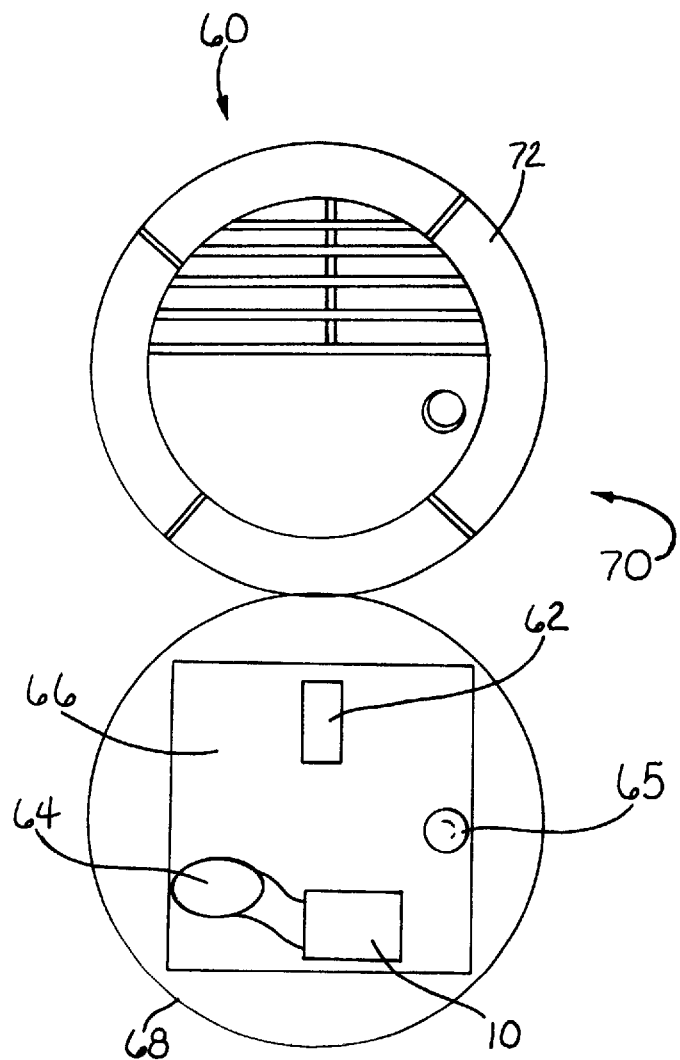
FIG. 13 is an illustration of a gas sensor device.

Referring to FIG. 13, there is illustrated a contaminant gas detector 60 including a sensor 40 or 50, a battery 62, a horn or buzzer 64, and/or an alarm device 63, such as an indicator light 65, and interconnecting circuitry all mounted on a circuit board 66 securely attached within a base 68 of casing 70. A lid 72 is pivotally mounted to base 68 to close the casing 70. The detector 60 can be installed in a convenient location and transmits an audible warning or alarm signal through horn 64 or flashes of light with light 65 when a contaminant gas is sensed. It is also within the terms of the invention, to transmit the signal to a controller (not shown), to activate a remote alarm and/or an air exhaust.

Another aspect of the invention relates to a permselective filter or membrane layer, i.e., a gas selective barrier, 48A, 48B,52 constructed of a material that provides for molecular specificity such that certain gases, i.e., CO, pass through the membrane layer, but interfering gases such as IPA, are restricted, rejected, removed or chemically reacted. The permselective filter layer 48A,48B,52 is selected from a group of filter elements constructed of microporous, nanoporous, nonporous, or chemically reactive materials. For example, the filter element can be a polymer membrane selected from the group comprising cationic membranes, anionic membranes, and bipolar membranes. The cationic membrane can be comprised of sulfonic acid groups. The porous polymer membrane can also comprise a molecular sieve dispersed throughout an inert polymeric support. In another embodiment (discussed below), the porous membrane is a zeolite powder dispersed throughout a nonporous, inert polymeric support. The nonporous, inert polymeric support can be a layer of material selected from the group consisting of Nafion®, Teflon®, polypropylene, polyethylene, and cellulose. The nanoporous membrane is constructed from nanoporous alumina or polysulfone or regenerated cellulose on a polymeric support. The layer of nonporous membrane is selected from the group comprising celulose triacetate, polyesters, vinyl polymers, latex polymer, polysulfone, polyethylene, cellulose, polystyrene, polymethacrylates, polynitriles, polydienes, polyoxides, polyesters, polysiloxanes, polyamides, Nafion®, Teflon®, Kynar®, polypropylene, and tetra polymers, and trifluoro polymers.

Examples of different membrane or filter layer materials include microporous membranes with very small pores, in the range of 0.04 to 0.19 micron, available from the Hoechst Celanese Corporation of North Carolina, nanoporous ultrafiltration membranes such as PLAC-Cellulose membranes available from Millipore Corp. of Maine, nonporous or solid membranes such as layer of nonporous membrane is selected from the group consisting of celulose triacetate, polyesters, vinyl polymers, latex polymer, polysulfane, polyethylene, cellulose, polystyrene, polymethacrylates, polynitriles, polydienes, polyoxides, polyesters, polysiloxanes, polyamides, Nafion®, Teflon®, Kynar®, polypropylene, and tetra polymers, and trifluoro polymer membranes available from most plastic film companies, and a layer of chemically reactive materials (discussed below) such as those available from Barneby and Sudcliff Co. of Ohio and Calgon Carbon Co. of Pennsylvania. Compounds, such as potassium permanganate, could be used as part of the filter to form a chemical filter. The permanganate would react with the interferences but allow the analyte to pass. Any or a combination of these films could be incorporated as a layer or zone in a multilayer package. Their overall function is to provide selectivity and thus provide a filter material.

The filter or membrane layer could be used to construct filters 48A, 48B of FIG. 11 or filter 52 of FIG. 12. The material is formulated by incorporating compounds in a membrane that allow a particular analyte to pass through the membrane while excluding potential interferences. In one embodiment of a membrane, zeolite powder is mixed with a polymer. The zeolite powder includes zeolite W, chabazite, erionite, potassium erionite, calcium zeolite A, sodium zeolite A, potassium zeolite A, and lithium zeolite A. Based on test results described below, unmodified zeolite powder, by itself, will not allow a small gas molecule to pass while at the same time inhibit the passing of larger molecules, that is, become a selective barrier. Further, as shown by test results described below, a thermosetting polymer, such as polyvinylidene fluoride (also known as Kynar®), forms a thin polymer membrane. However, the polymer membrane, by itself, will not selectively allow small gas molecules to pass therethrough while excluding unwanted large gas molecules.

An unexpected result was achieved by forming a membrane from mixtures of zeolite powder and a thermosetting polymer. The resulting membrane will selectively allow small toxic gas molecules, such as carbon monoxide, to pass through the membrane while excluding larger interfering gas molecules, such as isopropyl alcohol. Below are described examples and test results of zeolite membranes which demonstrate these properties.

Figure 14:
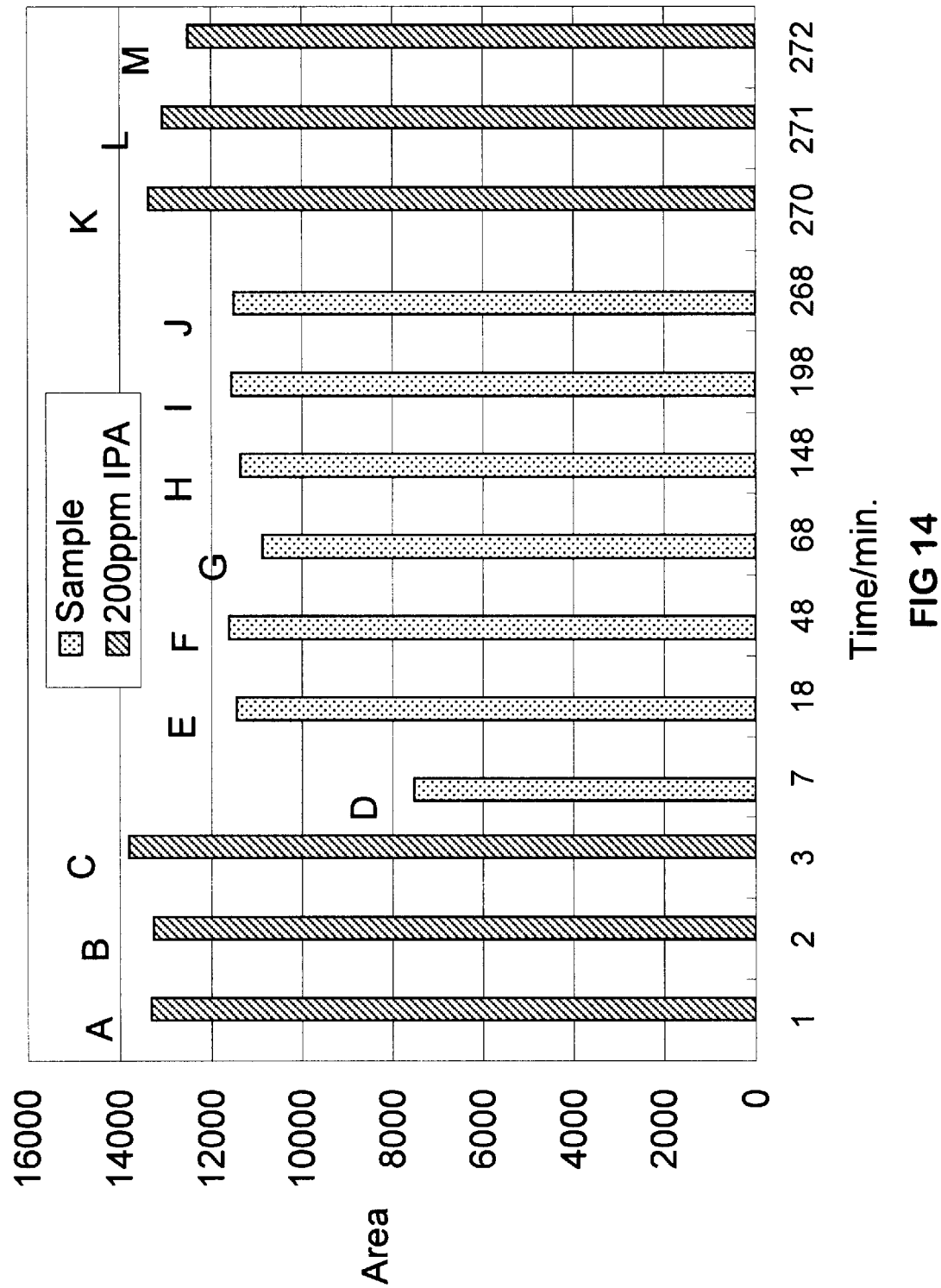
FIG. 14 is a chart showing the test results of a contaminant gas exposed to Zeolite.

Referring to FIG. 14, the results of an experiment to show that powder zeolite alone does not act as a high capacity absorber of isopropyl alcohol (IPA) is shown. In this experiment, ten grams of zeolite (Baylith W) are placed in a 500 mL florence flask. The flask is sealed with a septum and the enclosed air is purged by injecting a gas containing 200 ppm of isopropyl alcohol (IPA). The gas space above the zeolite is periodically sampled and subjected to gas chromatographic (GC) analysis. A plot of the area of the peaks (proportional to the quantity of IPA in the gas) measured from the GC analysis versus time is shown in FIG. 14. The first three peak areas corresponding to gas samples A,B,C (from 0–3 minutes) were directly from gas analysis of 200 ppm IPA gas to provide a calibrated reference peak. The next and subsequent peak areas, gas samples D–J (from 7–268 minutes) were from a gas analysis of the gas in the flask headspace. The last three peak areas K,L,M were again from a gas analysis of a calibrated gas of 200 ppm IPA gas. This graph shows that only a small fraction of the IPA is absorbed, less than 10%. This amount would not be enough to account for the zeolite in a membrane to act as an absorber.

In another test, a zeolite polymer membrane was shown to act as a selective filter. The membrane was formulated from a mixture 1.68 grams of zeolite (Baylith W) with 4.05 grams of polyvinylidene fluoride ("Kynar"). Approximately 0.5 grams of the above mixture (24% wt/wt zeolite) was placed between a heating assembly of two aluminum heating plates with approximately 10 drops of acetone and warmed to 140° C. The assembly was pressed at about 3000 pounds per square inch (psi) for 60 seconds, allowed to cool, and the resulting zeolite PVDF membrane removed from the aluminum plates. The resulting membrane was 0.225 mm thick.

To test for the effectiveness of a zeolite polymer membrane, two solid-state, carbon monoxide sensors 40, of the type illustrated in FIG. 11, were placed in a Figaro box 18, as shown in FIG. 6. One of sensors, designated as sensor A had a zeolite-PVDF membrane filter covering both the sensor and reference electrodes. The other sensor designated as sensor B had a PVDF membrane filter covering both the sensor and reference electrodes. The PVDF membrane was prepared by placing approximately 0.7 grams of polyvinylidene fluoride on aluminum plates, as previously described, with around 5 mL of acetone. The mixture was pressed at 3000 psi between heated plates at 140° C. for 60 seconds and a membrane with a thickness of 0.105 mm resulted. The sensors A and B were electrically connected to a National Instruments interface card in a computer 36. Potentials were recorded to computer 36 using custom software written via LabView for Windows. Open circuit potentials were monitored every 30–60 seconds and written to disk.

Figure 15:
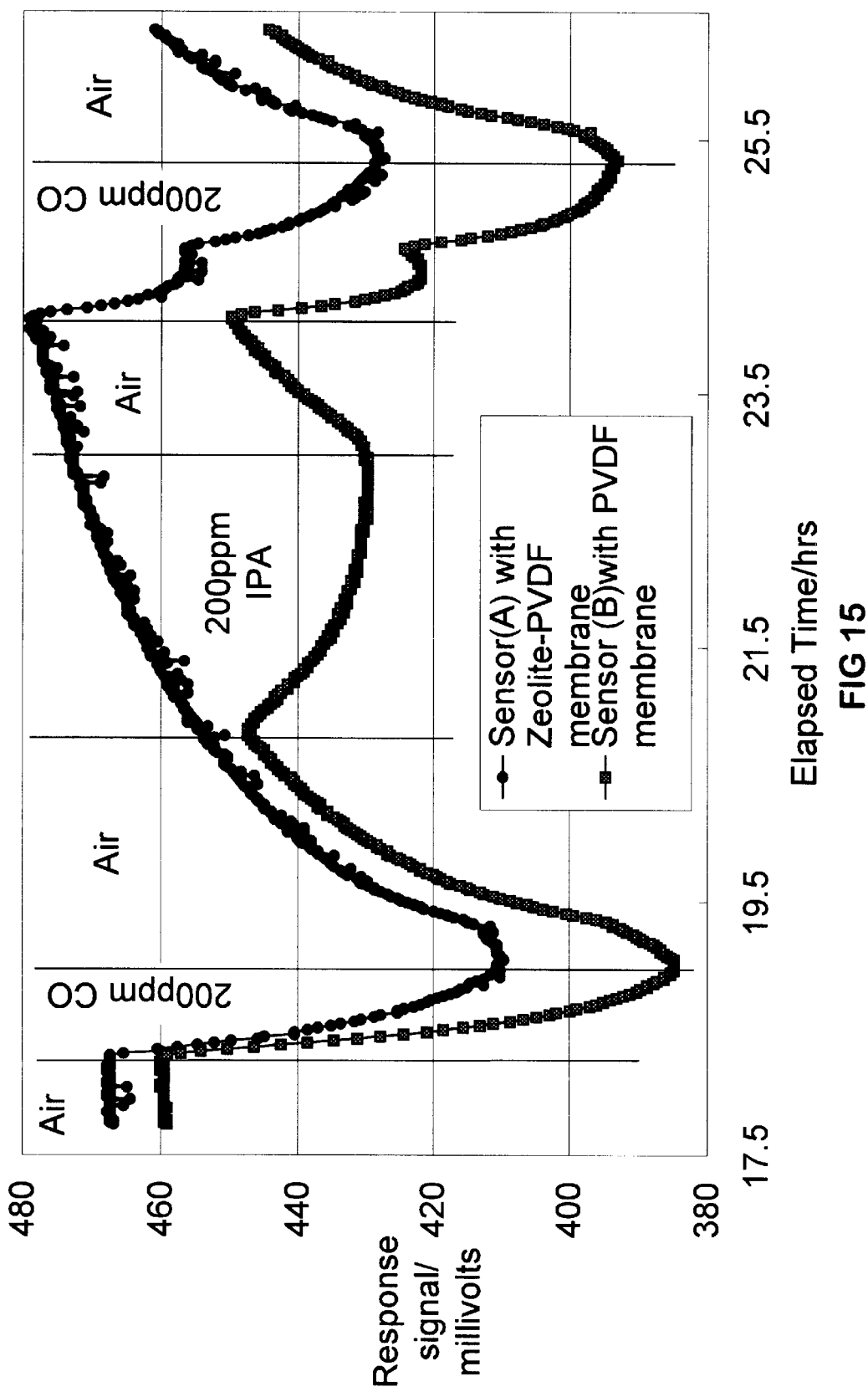
FIG. 15 is a graph showing the test results of two solid state sensors according to the present invention, one covered with a control membrane and the other covered with a Zeolite membrane, exposed to sample gases containing CO, air or IPA.

Sensors A and B in box 18 were subjected sequentially to an environment of air, 200 ppm CO, air, 200 ppm IPA, air, 200 ppm CO, and finally air. FIG. 15 shows the trace for the response signals versus time for sensors A and B. During the initial exposure to CO, both sensors give a response signal. However, when the sensors were subjected to 200 ppm IPA, there was a significant response signal from sensor B covered by the PVDF membrane filter while sensor A covered with the zeolite-PVDF membrane filter did not output a significant response signal. Since sensor B, covered by the PVDF membrane filter, outputs a significant signal in response to both the carbon monoxide as well as the IPA vapors in the atmosphere being tested for carbon monoxide, sensor B gave a false signal. This test indicates that the zeolite-PVDF membrane effectively blocked large molecules of the IPA while the PVDF membrane, by itself, allowed both the small CO molecules and the large IPA molecules to pass therethrough.

Figure 16:
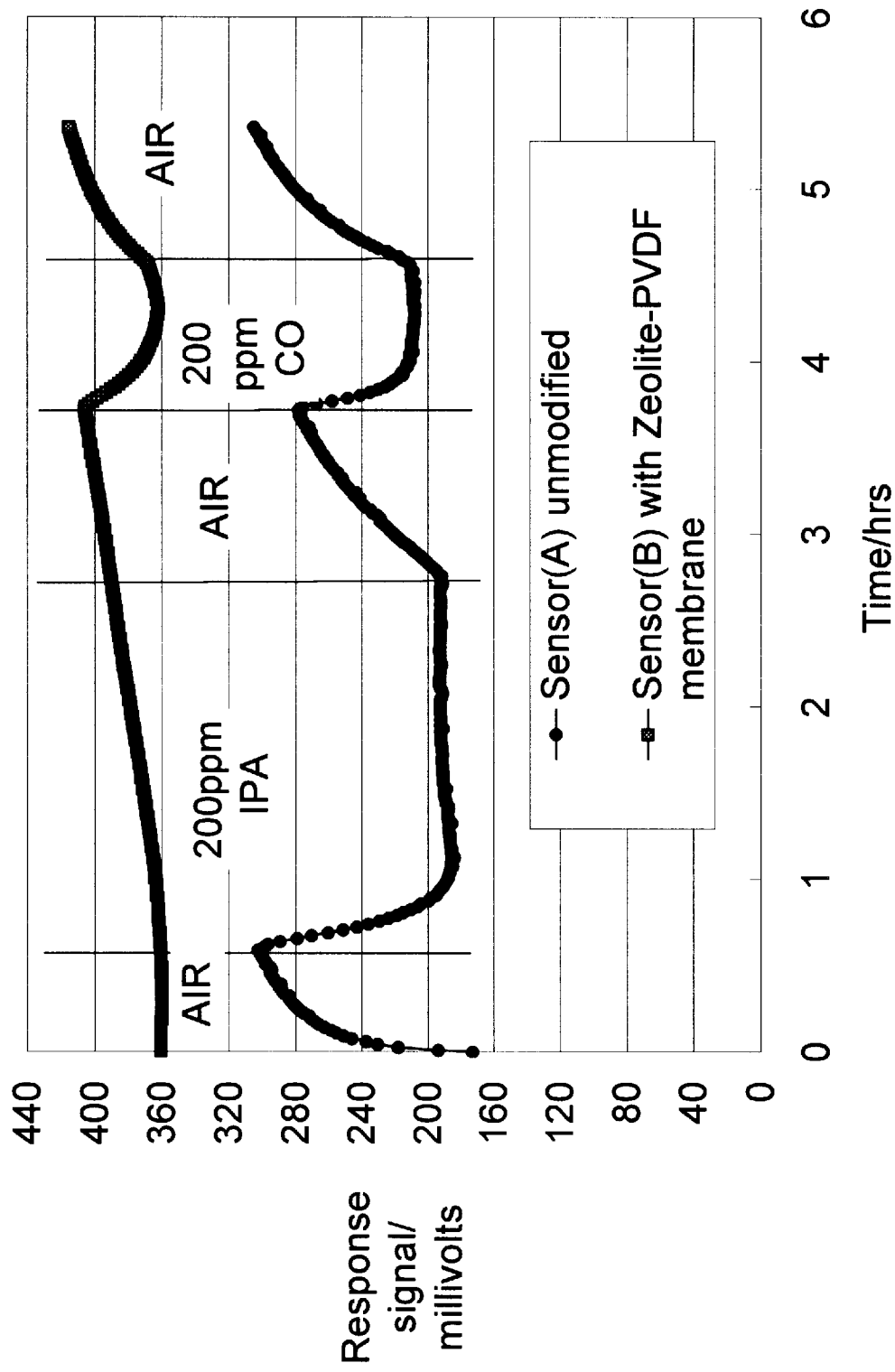
FIG. 16 is a graph showing the test results of two solid state sensors of the present invention, one covered with a Zeolite membrane and the other uncovered, from exposure to a sample gas containing either CO, air, or IPA.

FIG. 16 shows the results of a test similar to that shown in FIG. 15 only sensor A is unmodified, i.e. does not have a filter as shown in FIG. 1, and sensor B has been modified by adding a filter layer of zeolite-PVDF membrane to both sides of the solid state sensor 40, as shown in FIG. 112. Upon exposing sensors A and B to 200 ppm of IPA vapors, the unmodified sensor A immediately responds while the sensor B with the zeolite-PVDF membrane does not respond other than with a slow drift in a positive direction. Then air is injected into box 18 and both sensors A and B show an output signal corresponding to the signal when first exposed to air before the IPA was injected. Continuing, air with 200 ppm CO is injected into the chamber of box 18 and both sensors A and B output a signal indicating the presence of the 200 ppm of CO. This test demonstrates that a zeolite-PVDF membrane will selectively allow only small molecule toxic gasses, such as carbon monoxide, to pass through the membrane for sensing by the sensing electrode while excluding larger interfering gas molecules, such as isopropyl alcohol. The previous test demonstrates that a membrane of only polyvinylidene fluoride (PVDF) does not show molecular discrimination between carbon monoxide and IPA vapors. However, a simple mixture of polyvinylidene fluoride and zeolite yields a surprising result, i.e., a membrane that is selective for CO.

Other examples of filter membranes which can be used in conjunction with the gas sensor include polymers which reject molecules of IPA while letting molecules of CO in a sample gas to flow through to the sensor based on significantly different permeabilities i.e. permselectivity. Examples are membrane layers of Nafion®, Teflon®, cellulose, cellulose triacetate, latex, vinyl films, Kynar®, polyesters vinylpolymers, latex polymers, cellulose, polystyrene, polymetharcylate, or porous membranes such as Celgard available from Hoechst Celanese Co. of Charlotte, N.C.

While the gas sensor of the first embodiment previously described is effective to measure volatile gas contaminants in an atmosphere being monitored, it is also desirable to provide an additional embodiment of a gas sensor 100 that is multifunctional and can be constructed of multiple layers for sensing of humidity, temperature, pressure, as well as the presence of contaminant gases. The multiple layers (described below) can also function as spacers, adhesives for assembly, electrical connections, etc. While gas sensor 100 typically uses humidity, pressure, and temperature measurements for automatic compensation of the gas sensor in an environment where these variables are changing, the sensor can also be used for independently measuring humidity and temperature and pressure apart from measuring volatile gas contaminants.

For measuring conditions requiring continuous and long-term monitoring, gas sensor 100 operates as a stable, reliable gas sensor capable of both selectivity and automatic compensation for changes in environmental variables such as temperature, humidity, and pressure. For these applications, sensor 100 provides multiple functions, i.e., measuring the presence of a gas analyte, the temperature, the humidity, the pressure, etc. and can be constructed from multiple layers, whereupon in each layer a function or functions can be measured.

Figure 17:
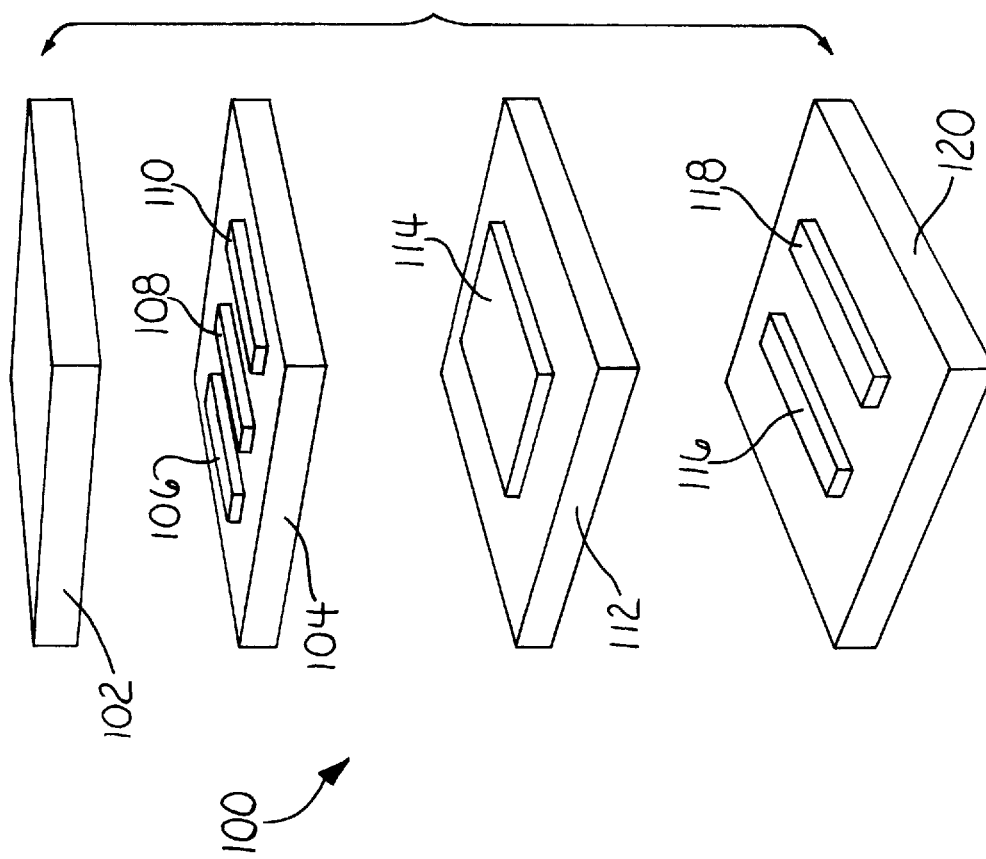
FIG. 17 is an exploded illustration of a multilayer, multifunctional gas sensor device.

FIG. 17 shows a schematic of a multiple function, multiple layer sensor device 100. Sensor device 100 includes a top filter layer 102 which provides a barrier to gaseous interferences, such as for example, isopropylalcohol. Layer 102 could be constructed from a membrane, such as filter membranes 48A, 48B of FIG. 11 or filter 52 as previously disclosed, or a chemical filter consisting of charcoal absorber impregnated with an oxidizing agent such as potassium permanganate, as described below. Below filter layer 102 is a conductive substrate 104, such as an electrode layer constructed of an electrolyte comprising an ionic polymer or a solid state electrolyte, such as for example, the commercially available Nafion®, Neosepta®, and Raipore® membranes or other structures similar to those described with regard to catalytic electrode 12 of the embodiment described before. A plurality of gas sensing elements 106,108,110 (108–110) each of which could sense one or more of the contaminant gasses listed previously with regard to the first embodiment are fixed onto ion-conductive substrate 104.

A reference substrate 112 is disposed below substrate 104 and is constructed of a similar material as ion-conductive substrate 104. A reference element 114 is mounted to the top side of reference substrate 112 and is sandwiched between reference substrate 112 and ion-conductive substrate 104. While one reference substrate 112 is illustrated in FIG. 17 as being assembled with a single conductive substrate 104, it is within the terms of the invention to incorporate additional conductive substrates. Moreover, reference element 114 can be attached to either side of reference layer 112 or even the bottom side of 104 since the location of reference element 114 is not critical to the function of the sensor 100. Finally, two additional sensing electrodes 116 and 118, discussed in more detail below, are depicted as being sandwiched between reference substrate 112 and a porous inert layer 120. Sensing electrodes 116 and 118 each output a voltage signal. The output voltage signals are proportional to the pressure, temperature, relative humidity, or any other environmental variable that requires monitoring. A porous, inert protective layer 120 which covers sensing electrodes 116 and 118 is constructed of porous polypropylene or porous polyethylene, for example Celguard available from the Hoechst Celanese Co. of Charlotte, N.C. or one of a combination of the permselective barriers previously described.

Figure 18A:
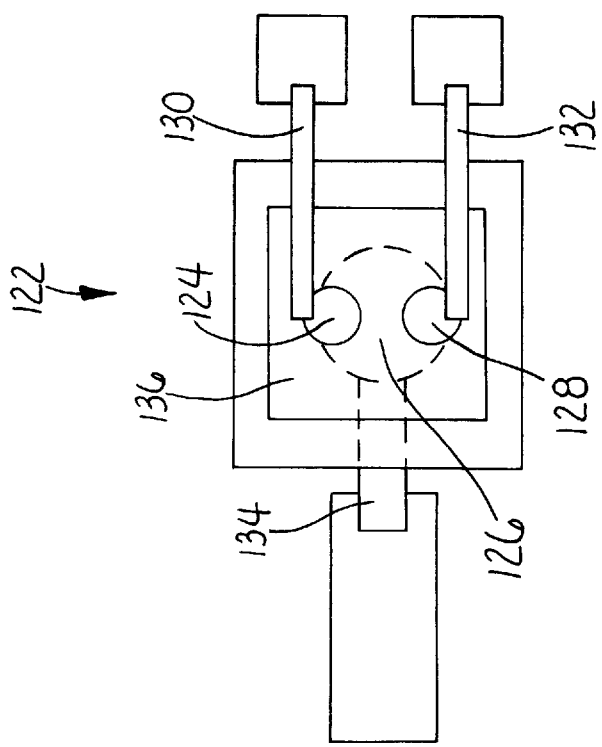
FIG. 18A is a view through line 18A—18A of FIG. 18.
Figure 18:
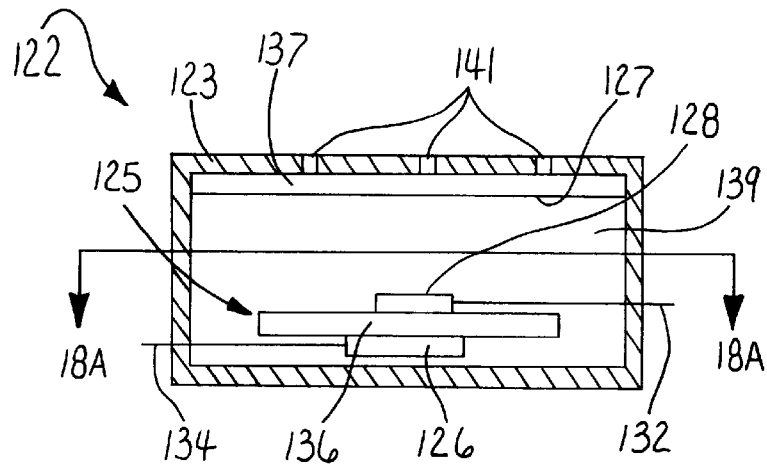
FIG. 18 is a side view in cross section of another embodiment of an exemplary multilayer, multi-functional gas sensor device.

Referring to FIGS. 18 and 18A, there is illustrated an example of a multiple function, multiple layer, CO sensor 122. Sensor 122 has a housing 123 with a plurality of openings 141 through the top section to allow the sample gas of the surrounding atmosphere to flow into the interior of the housing. The sensor includes an electrode assembly 125 with three electrodes 124, 126, and 128 encased within housing 123. Electrode 124 is a CO sensing electrode constructed of a platinum catalyst and electrode 128 is a temperature/% relative humidity (RH) compensator electrode. Electrodes 124 and 128 are mounted on one side of a conductive substrate 136 formed of the same material as conductive substrate 104. A reference electrode 126, constructed of desired material such as a silver/silver ion, is mounted on an opposite side of conductive substrate 136 from electrodes 124 and 128. Electrical contact members 130, 132, and 134 extend outward from CO sensing electrode 124, temperature/% RH compensator electrode 128 and reference electrode 126, respectively, and have pads on their free ends for attachment to a computer or electrical meter. A membrane or filter 127 extends across the casing 123 and divides it into upper and lower chambers 137 and 139, respectively. All of the gas being tested must pass through the openings 141 in the top cover of casing 123 and into the upper chamber 137. Then the gas sample flows through the membrane 127 prior to being exposed to electrode assembly 125 located in the lower chamber 139.

In operations, sensor 122 outputs a voltage signal from sensor electrode 124, reference electrode 126, and compensator electrode 128 to a computer, such as computer 36 described above, through voltage measuring circuitry (not shown). The voltage output from the compensator electrode 128 can be subtracted from the voltage output of the sensor electrode so that the output from the sensor electrode does not reflect changes in temperature and relative humidity. As in the embodiments described before, the output from the sensor 122 can indicate the presence of a containment gas such as CO.

There are two approaches for selecting the temperature/% RH compensator electrode 128. In a first design, as shown in FIGS. 18 and 18A, the temperature/% RH compensator electrode 128 is constructed of a material, such as carbon, carbon with silver deposited onto its surface, or other metals inert to CO. Electrode 128 outputs a voltage signal proportional to changes in both temperature and % RH that is substantially equal to the voltage signal output of CO sensing electrode 124 in response to the same changes in both temperature and % RH. However, the material from which the temperature/% RH compensator electrode 128 is made does not output a voltage signal in response to the presence of CO as with the CO sensing electrode 124. An example of this type of temperature/% RH compensator electrode is a gas diffusion electrode (GDE) Model No. EFCG, "S" Type on TGPH-10 Toray Paper, with 10% (wt) silver per carbon, and 0.5 mg/cm$^2$ silver loading available from E-TEK, Inc. of Natick, Mass.

Figure 19:
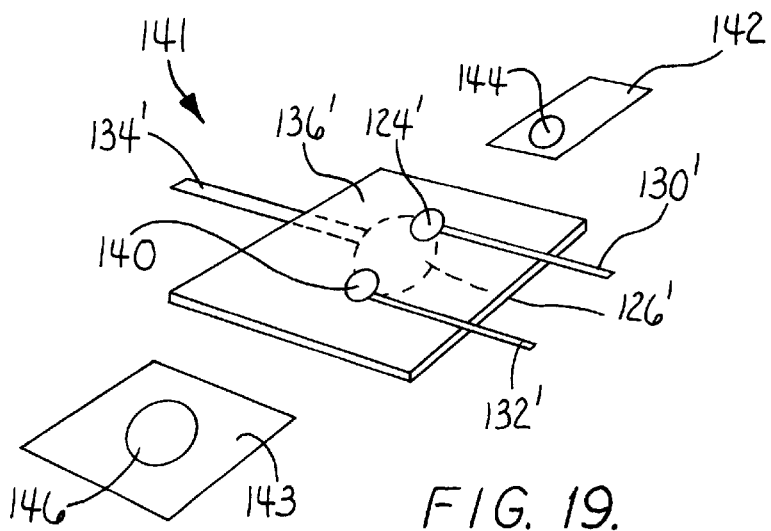
FIG. 19 is an exploded illustration of the sensor assembly for the gas sensor device of FIG. 18.

In a second design, as shown in FIG. 19, a sensor device 141 is constructed with the material for the Temperature/% RH compensator electrode 140 formed of the same material as the CO sensing electrode 124'. In that case, the Temperature/% RH compensator electrode 140 would be completely isolated from the surrounding atmosphere while the reference electrode 126' would be exposed to the environment being sampled to allow the voltage signal output of electrode 126' to reflect changes in the surrounding atmosphere. Although electrode 140 is isolated from the sample gas, the water vapor in the sample gas being sampled saturates the conductive substrate 104 (which does not allow the contaminant gas molecules to flow through) and is exposed to the electrode 140, which in turn, outputs a voltage signal corresponding to the relative humidity and temperature of the sample gas. The result is that the change in the voltage signal output of the Temperature/% RH compensator electrode 140, in response to changes in both temperature and % RH, is substantially equal to changes in the voltage signal output of CO sensing element 124' without accounting for the output voltage signal of the CO sensing element in response to the presence of either CO or isopropylalcohol. Then, the voltage output of CO sensing element 124' can be compensated by subtracting the voltage signal of electrode 140 so that the sensor output does not reflect changes in temperature and relative humidity.

The sensor device 141 is constructed of two platinum-containing gas diffusion electrodes 124' and 140 mounted to one side of a conductive substrate 136' formed of a rectangular piece of Nafion® 117 by means such as pressure bonding, heat bonding, ultrasound welding, heat sintering, solvent bonding, inert polymer "gluing", or making the electrodes an integral part of the substrate by depositing metal electrodes into or onto substrate 136'. A silver/silver ion reference electrode 126' is attached to the opposite side of the Nafion® 117 substrate 136' by conventional means described before. Electrical connectors 130', 132' and 134' are then attached to electrodes 124', 140, and 126', respectively, and temporarily fixed in place for testing purposes with two strips 142 and 143 of cellophane tape available from 3M Corp. of St. Paul, Minn. The first strip 142 has a hole 144 and is placed over the CO sensing electrode 124' and the Temperature/% RH compensating electrode 140 and is attached to the upper side of substrate 136' so that the hole 144 is aligned with electrode 140 to allow access to the atmosphere being sampled for compensation of variations in temperature and % RH. The second strip of tape 143 has a hole 146 therethrough and is attached to the lower side of substrate 136' so that the hole 144 is aligned with reference electrode 126' to allow access to the atmosphere being sampled. This configuration illustrates the strategy of employing two CO sensing electrodes 124' and 140, blocking one off, i.e., electrode 124' which functions as the CO electrode, from the environment to be sampled, and using this blocked electrode in combination with an exposed reference electrode 126' to determine voltage outputs proportional to changes in the ambient temperature and humidity.

To conduct a test of sensor 141, the sensor was placed in a test setup (not shown) incorporating a Figaro box, of the type shown in FIG. 6, with temperature and relative humidity measuring devices located in the measuring chamber of the box. The electrical connectors 130', 132', and 134' from the electrodes 124', 140, and 126', respectively, were electrically connected to electrical connectors in lid 28 and the box 18 was sealed with the clamped lid 28. The electrical connectors from the lid were then connected by wires to a National Instruments interface card mounted within a conventional PC computer 36.

Figure 20:
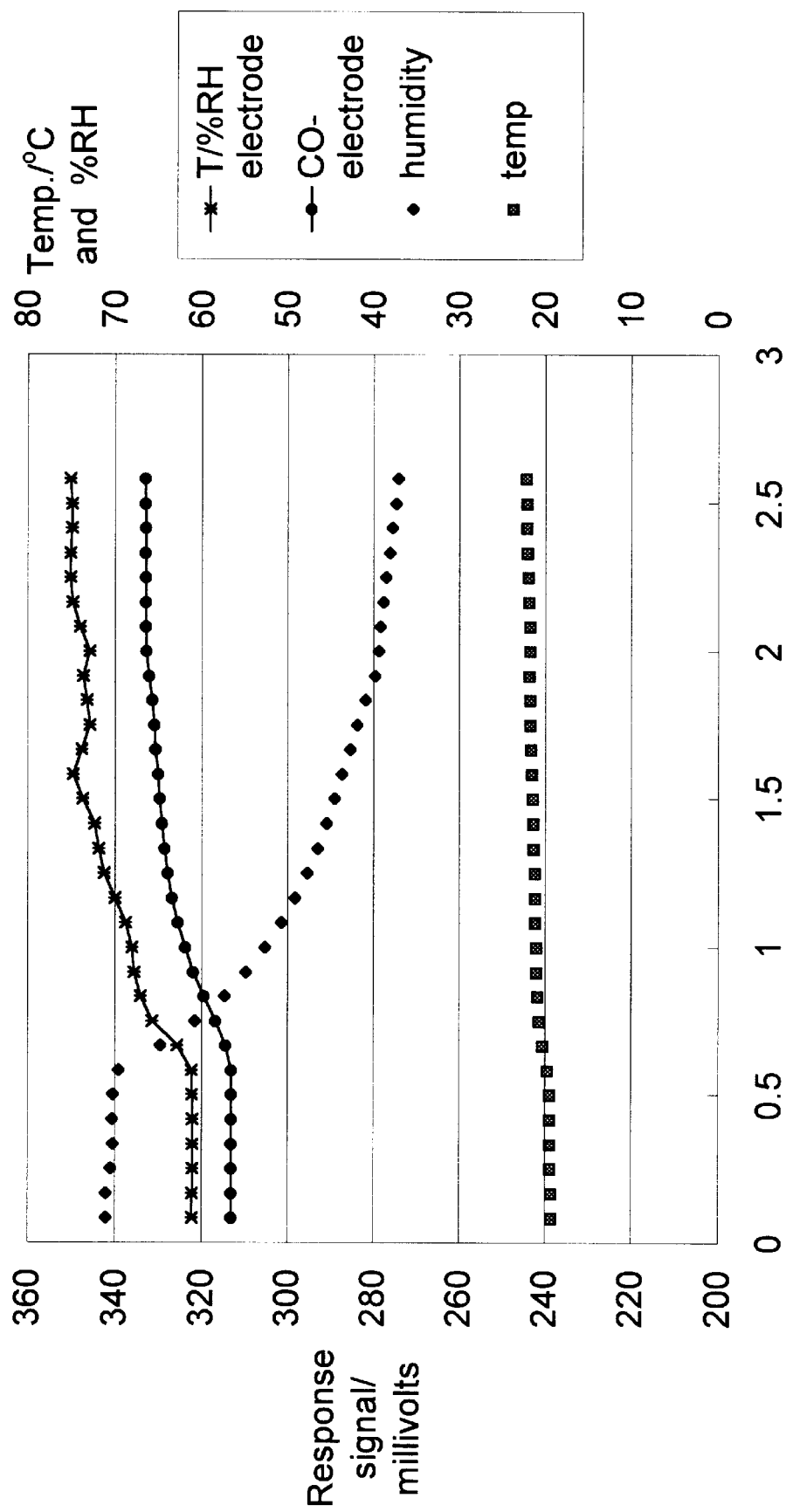
FIG. 20 is a graph showing four traces corresponding to temperature, relative humidity, the output of a CO sensor, and the output of a temperature/% RH element generated by exposing the multilayer, multifunctional gas sensor of FIG. 18 to a sample gas having a changing relative humidity.

FIG. 20 shows the response of sensor assembly 141 of FIG. 19 in the Figaro box to exposure to cycles of humid and dry air at a relatively constant temperature. The four traces shown represent the output data corresponding to temperature, relative humidity, the CO sensor electrode 124', and the temperature/% RH electrode 140. During startup, from 0 to 0.6 hours, sensor 141 in the Figaro test box was subjected to a stream of sparged (fully saturated) air. After steady state is obtained, dry air is fed into the box and the relative humidity drops from about 70% RH to about 37% RH during a period of two hours. The voltage outputs of the CO electrode 124' and the T/% RH electrode 140, as shown in the trace in FIG. 20, shows an increase of approximately 30–40 mV when % RH goes from 70% to 37% RH.

Figure 21:
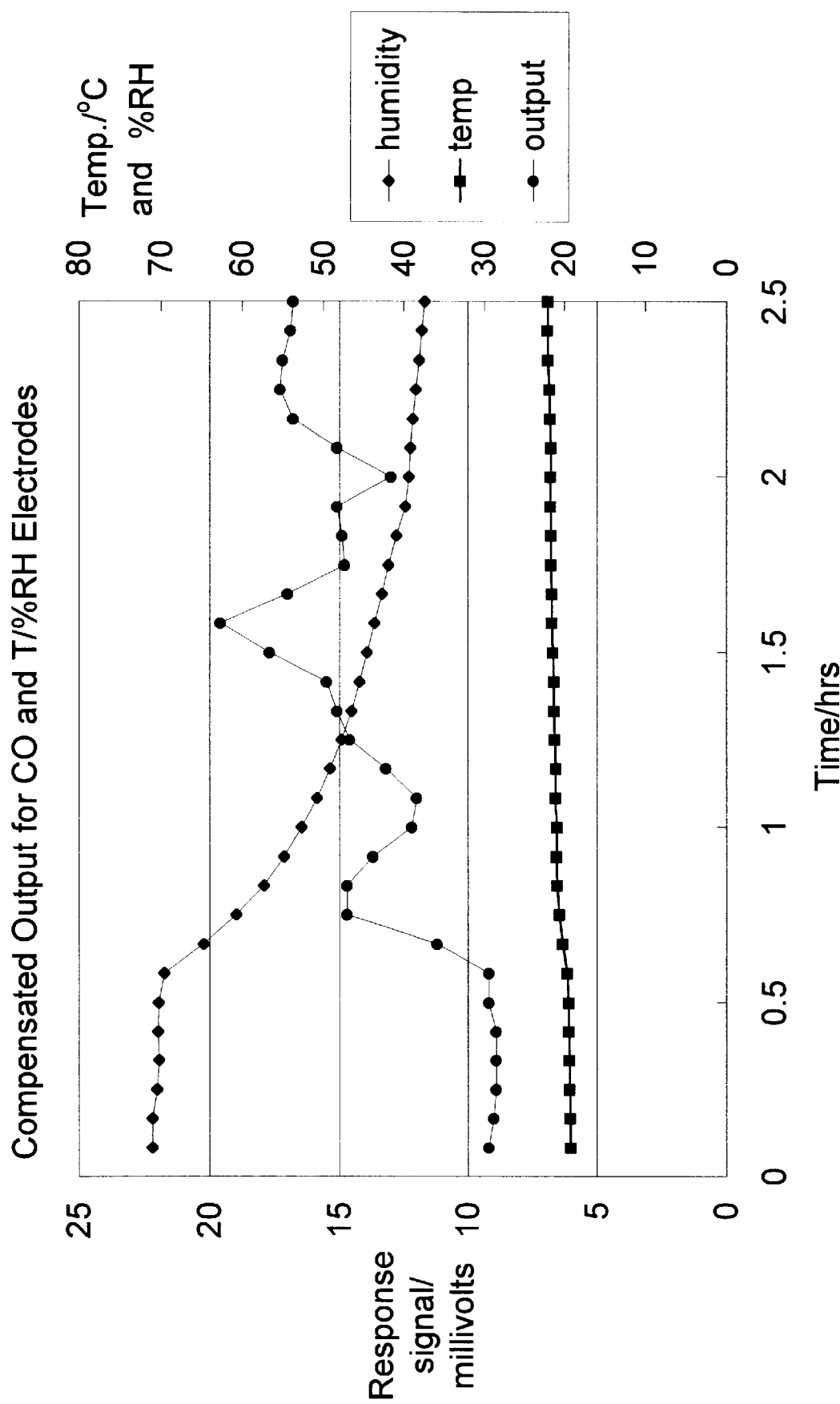
FIG. 21 is a graph showing the compensated output for CO and temperature/% RH electrodes.

FIG. 21 shows a trace of the corrected output, i.e., the difference between the voltage outputs of the CO and T/% RH electrodes 124' and 140, respectively. From 0 to 0.6 hours, during the period when the ambient temperature and relative humidity are substantially constant, there is a slight offset of 9 mV. This is due to small differences in the electrodes or electrical connections to the electrodes. At approximately 0.6 hours, when the dry air is introduced into the Figaro box, the output of the device 141 is now compensated as evidenced by an average shift of only about 5 to 8 mV in the output voltage. This shift is relatively insignificant when compared with the 50–180 mV changes expected when monitoring environments expected to contain between 30 and 400 ppm of CO. The importance of the test results shown in traces of FIGS. 20 and 21 is that the change in the voltage signal output of both the Temperature/% RH compensator electrode 140 and the CO sensing element 124', in response to changes in both temperature and % RH, is substantially equal.

Figure 22:
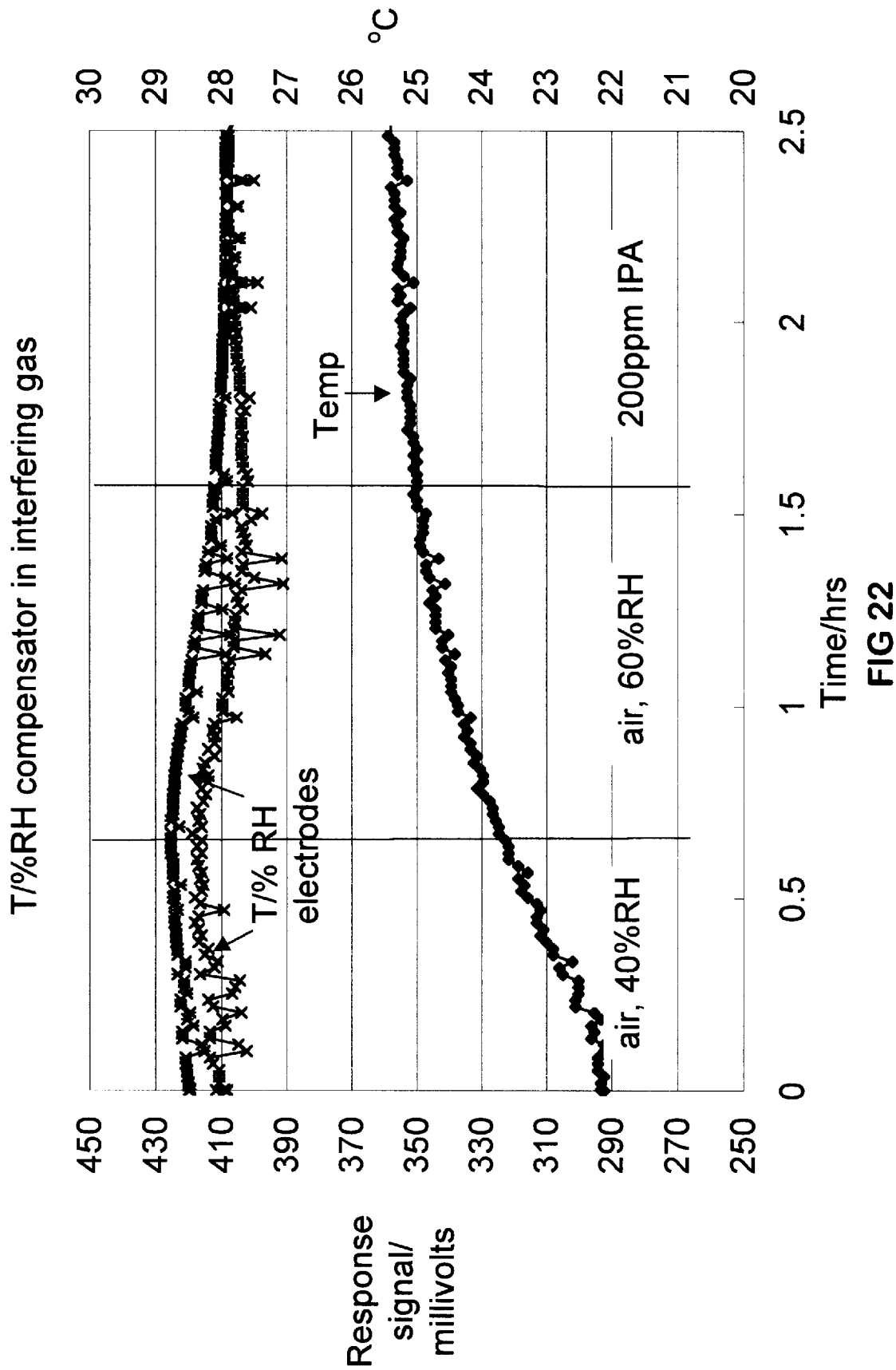
FIG. 22 is a graph of the output of a Temperature/% RH electrode exposed to an interfering gases.

An important aspect of the T/% RH electrode 140 is its ability to output a voltage signal that is invariant when in contact with potential interferences, such as isopropylalcohol. An insensitivity to interference gases in device 141 is achieved by covering the Temperature/% RH electrode 140 to the atmosphere being sampled, such as with a gas-impermeable film, while leaving the reference electrode 126' exposed to the atmosphere being sampled. The reference electrode 126' of silver ion/silver is insensitive to gasses such as carbon monoxide or isopropylalcohol. The Nafion® substrate 136' also provides a barrier to isopropylalcohol as well. This point is illustrated in FIG. 22 which shows a trace of the outputs of two T/% RH electrodes placed in a Figaro box and exposed to air at two different relative humidity levels for two consecutive periods of time and then to isopropylalcohol for a third period of time. During the first period of about 0.65 hours, the temperature rose from about 22.3° C. to about 23.5° C. and the relative humidity of the air was about 40% RH. During this first period, the voltage outputs of both T/% RH electrodes remained essentially the same. Next, during the second period of time from about 0.65 hours to about 1.5 hours, the relative humidity of the air was about 60% RH and the voltage outputs of both T/% RH electrodes still remained essentially the same. Finally, during the third period of time from about 1.5 hours to about 2.5 hours, the relative humidity of the air was still about 60% RH and the T/% RH electrodes were exposed to 200 ppm of IPA. During this final period of time, the voltage outputs of both T/% RH electrodes still remained essentially the same. The results of this test show that there is no evidence that the T/% RH electrodes respond to isopropylalcohol.

Figure 19A:
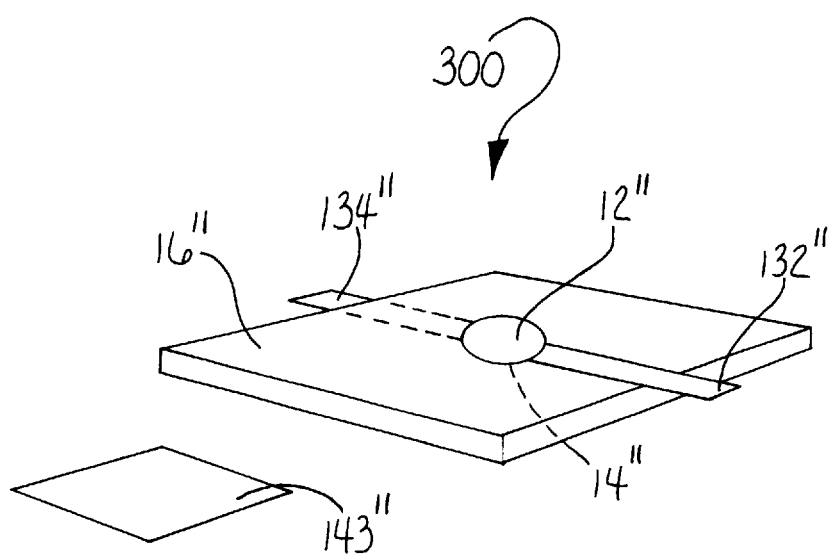
FIG. 19A is an exploded illustration of a modified sensor assembly adapted for use in the gas sensor device of FIG. 18.

Another embodiment of a sensor device as shown in FIG. 19A, which is similar to the sensor device 141 illustrated in FIG. 19, the sensor device 300 is constructed with a conductive substrate 16" having a CO sensing electrode 12" with an electrical connector 132" and a Temperature/% RH compensator electrode 14" with an electrical connector 132" mounted on either side. In this embodiment, the material for the Temperature/% RH compensator electrode 14" is formed of the same material as the CO sensing electrode 12". The Temperature/% RH compensator electrode 14" is completely isolated from the surrounding atmosphere by a strip of tape 143" while the CO sensing electrode 12" is exposed to the environment. With this embodiment, the Temperature/% RH compensator electrode 14" also functions as the reference electrode. Although electrode 14" is isolated from the sample gas being monitored, water vapor in the sample gas saturates conductive substrate 16" (which does not allow the contaminant gas molecules or CO to flow through). The water vapor is then exposed to electrode 14", which in turn, outputs a voltage signal through lead 134" corresponding to the relative humidity and temperature of the sample gas. Sensor 300 performs in a similar manner to sensor 141 illustrated in FIG. 19, except for the elimination of reference electrode element 126' which is unnecessary. The change in the voltage output of sensor 300 is measured as the difference of electrodes 12" and 14". The result is that voltage output of sensor 300 does not vary with changes in temperature or humidity but does respond to the presence of CO. This would be considered a form of automatic compensation since no additional processing of voltages is necessary.

Figure 21A:
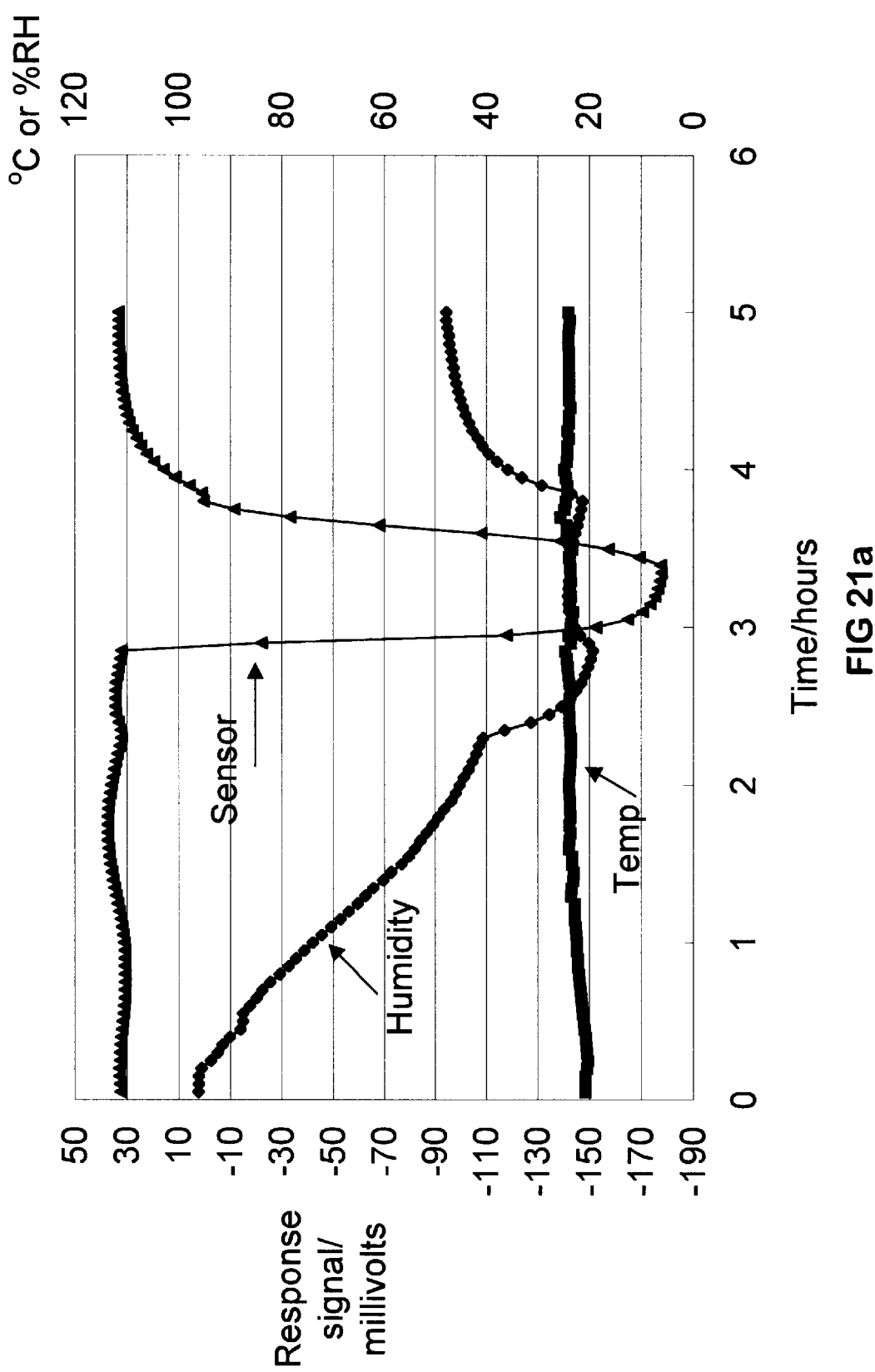
FIG. 21A is a graph showing the compensated output for a sensor device with automatic temperature and humidity compensation.

FIG. 21A shows a trace of the automatically corrected output of sensor 300, i.e., the difference between the voltage output of the CO electrodes 12" and 14", exposed to cycles of humid and dry air at a relatively constant temperature in a Figaro box. From 0 to 0.1 hours, there is a small 30 mV offset due to small differences in the electrical connections of electrodes 12" and 14". At approximately 0.1 hours, dry air is introduced into the Figaro box, and the output of sensor 300 is compensated as evidenced by almost no variation in the baseline of the sensor. At 2.75 hours, 200 ppm of CO is introduced into the Figaro box and a rapid response, i.e., the output changes from 30 to −180 mV, is recorded. Upon introducing air saturated with water into the Figaro box at 3.5 hours, the baseline returns to the value of 30 mV although the final humidity is different than the starting value (95% RH vs 47% RH). The importance of the test results shown in FIG. 21A is that the change in voltage signal is due only to CO and not changes in temperature or relative humidity.

Although the examples and figures show the compensated electrode or layer as an integral part of the sensor, it is also within the terms of the invention to construct a sensor with a separate compensated electrode.

Referring again to FIGS. 18 and 18A, the filter or membrane layer 127, is identical to the filter or membrane layer 48A, 48B of FIG. 11 or filter 52 of FIG. 12, and extends across the casing 123 and divides it into upper and lower chambers 137 and 139, respectively, as previously discussed. While the membrane 127 is effective for screening out large molecules of interfering substances, such as alcohols, while allowing the carbon monoxide to pass therethrough, it is also within the terms of the invention to use a chemical filter as one of the layers or zones of multilayer gas sensor. For this example, membrane 127 can be replaced with absorptive support such as carbons or alumina impregnated with strong oxidizers such as potassium permanganate. That is the casing 123 can be filled with a chemical filter which surrounds the electrode assembly 125. These compounds can oxidize interfering substances, such as the alcohols, while allowing the carbon monoxide to pass unreacted.

Figure 23:
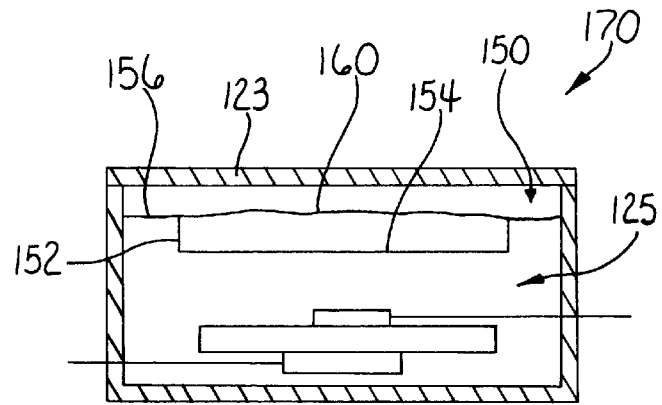
FIG. 23 is a side view in cross section of an embodiment of a multilayer, multi-functional gas sensor device incorporating a chemical filter.

Referring to FIG. 23, there is illustrated an example of a sensor device 170 which is essentially identical to sensor device 122 except that the filter 127 in casing 123 is replaced with a chemical filter 150 in accordance with the present invention. The chemical filter 150 can be constructed of a cup shaped support 152 having a meshed bottom surface 154 and support sides 156 extending outward from the cup support 152 and attached to the walls of casing 123 so that all air flow through the top of casing 123 must flow through cup support 152 to reach electrode assembly 125. A chemical mixture 158, as described below, is placed in cup 152 and covered with a porous cover 160 of Celgard from Hoechst Celanese, of Charlotte, N.C.

An exemplary chemical mixture of carbon impregnated with $KMnO_4$ can be prepared by forming a solution of 15 gms of $KMnO_4$ in 275 mL of deionized water. Three grams of a high surface area carbon, such as 7 Acres Aquarium filter carbon from Tetra/Second Nature, available from Willinger Brothers of Oakland, N.J., is next mixed into the solution. The carbon impregnated with $KMnO_4$ is filtered, dried, and ground to form a powder with a mesh of approximately 20–170 mesh units. Prior to assembling sensor device 170, the chemical filter 170 is mounted.

Figure 24:
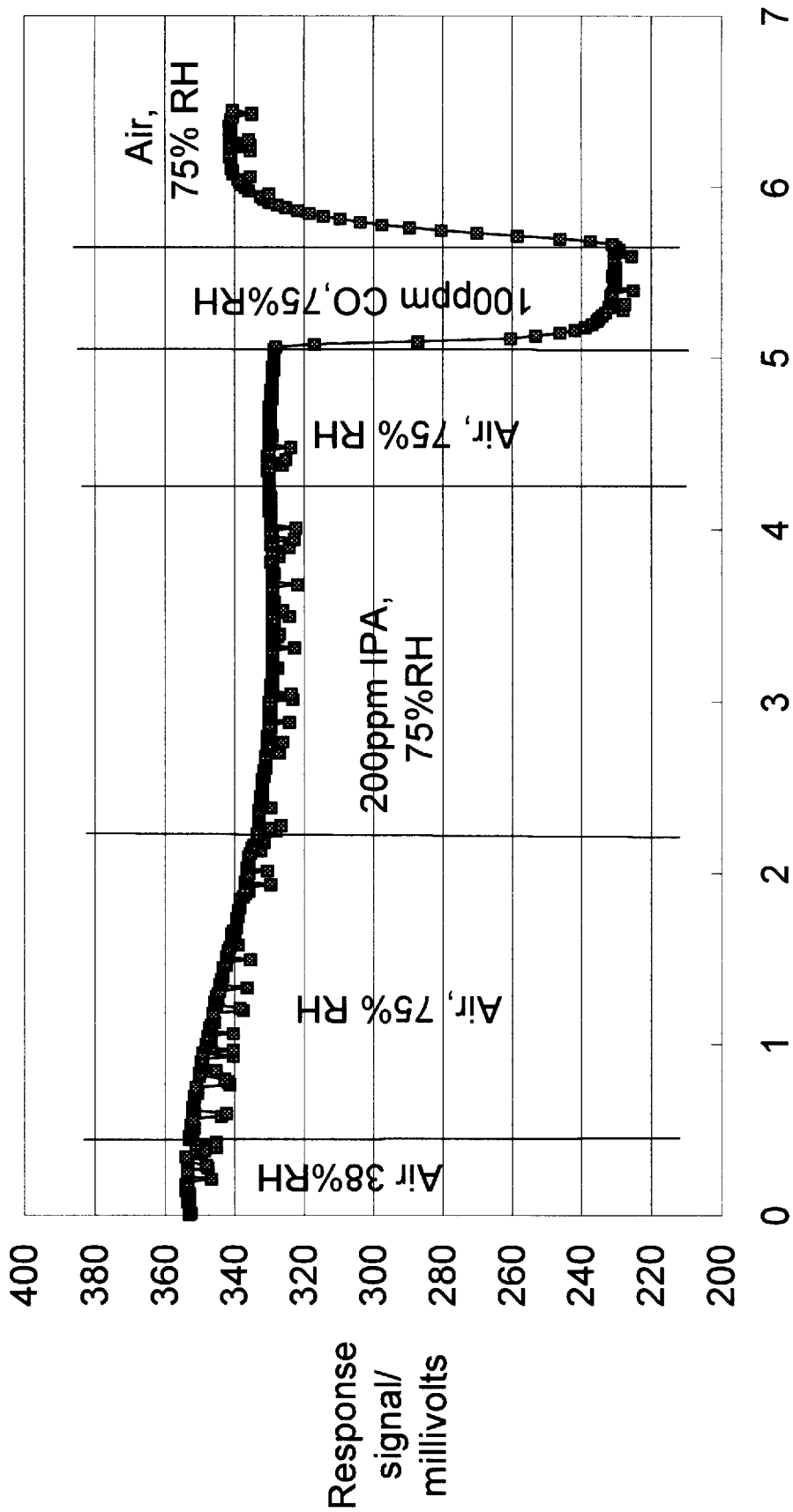
FIG. 24 is a graph of the test results of exposing a CO sensor device with a chemical filter to interfering gases.

FIG. 24 shows the response of sensor device 170 incorporating a chemical filter 150 in a Figaro box to six different gas environments during six different periods of time beginning with: humid air at 38% RH, humid air at 75% RH, humid air at 75% RH mixed with 200 ppm of IPA, humid air at 75% RH, humid air at 75% RH containing 100 ppm of CO, and humid air at 75% RH. During the first period of time from 0 to 0.5 hours, the output of sensor device 170 remains essentially constant. During the second period of time from 0.5 to 2.25 hours, the output of sensor device 170 shows a slight decrease in the output corresponding to an adjustment for the change in relative humidity. In the third time period between 2.25 hours and 4.25 hours, the output of sensor device 170 remains substantially constant even though the test sample contains a significant amount of IPA. This shows that the sensor device 170 is not effected by the presence of IPA due to the presence of the chemical filter. Continuing, in the fourth time period from 4.25 hours to 5 hours the IPA is removed from the Figaro box and replaced with humid air at 75% RH. Again the output of sensor device 170 remains substantially constant. In the fifth time period from 5 hours to 5.7 hours, sensor device 170 is exposed to humid air at 75% RH with 100 ppm of CO. An output signal is measured that rapidly achieves steady-state at a significant decrease from the other output signals showing the presence of CO. Finally, in the sixth time period from about 5.7 hours to 6.5 hours, the CO is flushed out of the Figaro box and sensor device 170 is exposed to humid air at 75% RH. Again the sensor device outputs a substantially constant response similar to that of the first four time periods. This test shows that the sensor device 170 is an effective means of detecting CO even in the presence of IPA.

Other chemically impregnated substances, such as alumina with permanganate or carbon with a mix of silver, copper, and/or high valent chromium salts would provide an effective chemical mixture to be incorporated in chemical filter 150.

Figure 25:
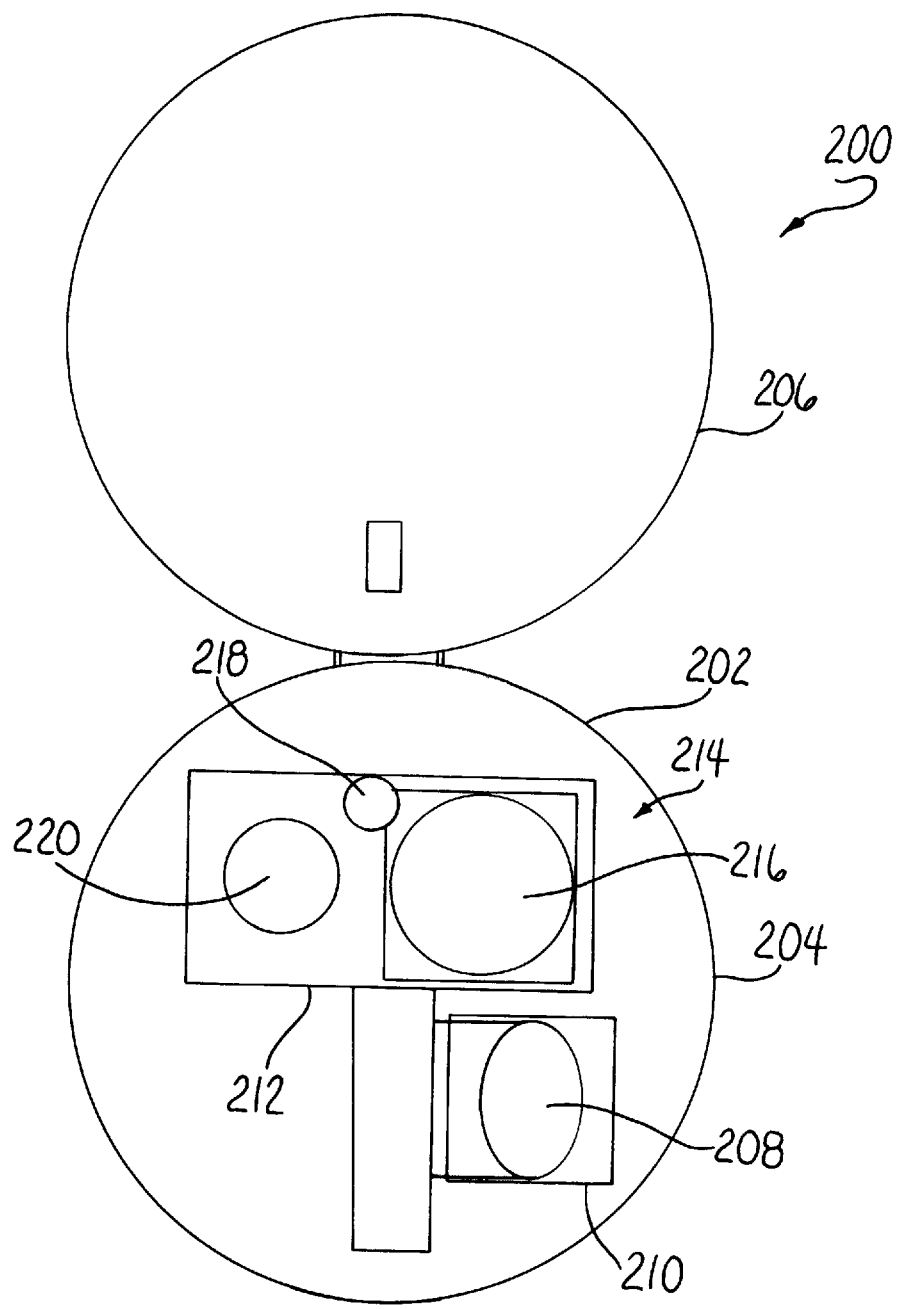
FIG. 25 is a schematic illustration of the multilayer, multifunctional gas sensor incorporated in a smoke detector.

Referring to FIG. 25, there is illustrated a smoke and gas detector 200 constructed with a housing 202 including a base 204 and a lid 206. The base 204 and lid 206 can have openings therethrough (not shown). Within the base 204 is mounted a sensor device 208 selected from the various types and embodiments described before for measuring a contaminant gas with or without temperature and relative humidity compensation. Sensor device 208 is mounted to a board 210 and connected to a battery powered circuit board 212 which contains control circuitry for operating an alarm 214, including a horn 216 and a light 218 in response to a signal from a smoke detector 220 or a signal from sensor device 208 indicating the presence of a contaminant gas, such as for example CO.

The patents listed herein are intended to be incorporated by reference in their entireties.

It is apparent that there has been provided in accordance with this invention apparatus and methods for testing low concentrations of gas contaminants with a sensor that satisfy the objects, means and advantages set forth hereinbefore. According to the invention, an electrochemical gas sensor is provided to measure volatile gas contaminants in an atmosphere being monitored, generally at ambient temperatures below 100° C. The sensor, constructed of a sensor electrode and a reference electrode on a separator, allows for exposure of both the sensor and the reference electrodes to the atmosphere which is sensed for gaseous contaminants. In an alternative embodiment, the sensors can be covered with a membrane filter which will selectively allow only small molecule toxic gases to pass through the membrane filters for sensing by the sensing electrode while rejecting or excluding larger interfering gas molecules. In another alternative embodiment, a multiple layer electrochemical gas sensor detects the presence of volatile gas contaminants in a sample gas as well as humidity, temperature, and/or pressure of the gas sample. The electrochemical gas sensor for measuring volatile gas contaminants can also be incorporated in a smoke alarm device.

While the invention has been described in combination with embodiments thereof, it is evident that many alternatives, modifications, and variations will be apparent to those skilled in the art in light of the foregoing teachings. Accordingly, the invention is intended to embrace all such alternatives, modifications and variations as fall within the spirit and scope of the appended claims.

What is claimed:

1. A potentiometric gas sensor for detecting the presence of a gas contaminant in a gas sample being monitored, said gas sensor comprising:

a first electrically conductive element which interacts with said gas contaminant when said first electrically conductive element is exposed to said gas sample;

a second electrically conductive element which does not interact with said gas contaminant when said second electrically conductive element is exposed to said gas sample; and an ion-conducting substrate having said first and second electrically conductive elements mounted thereon for ionic conduction between said first and second electrically conductive elements in support of the electronic conduction therebetween; and measuring circuitry connected to said first and second electrically conductive elements for comparing an electrical signal corresponding to the difference between first and second electrical signals generated by said first and second electrically conductive elements with a reference electrical signal.

2. The potentiometric gas sensor of claim 1 further including a filter layer through which said gas being sampled flows prior to being exposed to said first and second electrically conductive elements, said filter layer being a material selected from the group comprising microporous, nanoporous, and non-porous membranes, and chemically reactive materials.

3. The potentiometric gas sensor of claim 1 wherein said first electrically conductive element is a sensing electrode.

4. The potentiometric gas sensor of claim 3 wherein said second electrically conductive element is a reference electrode.

5. The potentiometric gas sensor of claim 4 wherein said sensing electrode has a different output response to said gas contaminant in said gas sample than said reference electrode.

6. The potentiometric gas sensor of claim 5 wherein said sensing electrode is constructed with a metal deposited onto a layer of material selected from the group comprising an ion-exchange membrane, an ion-conducting polymer, an organic polymer, an ion-conductive electrolyte, carbon, and a layer of fiber assemblies.

7. The potentiometric gas sensor of claim 6 wherein said ion-conducting polymer is selected from the group consisting of doped polyvinylchloride, polyphenyleneoxide, polyphenyleneglycol, polythiophenes, polypyrrols, polydibenzocrown ethers, polyphenylenes, substituted polyacetylenes, doped ceramic material and combinations thereof.

8. The potentiometric gas sensor of claim 6 wherein said organic polymer is selected from the group consisting of free acid functionality, totally neutralized acid functionalities, partially neutralized acid functionalities, amine functionalities, totally neutralized amine functionalities or partially neutralized amine functionalities, carboxylic acid, quaternary ammonium functionalities, and ionically doped polymers.

9. The potentiometric gas sensor of claim 1 wherein said first and second electrically conductive elements are spaced from each other and disposed in side by side relation to each other on said ion-conducting substrate.

10. The potentiometric gas sensor of claim 1 wherein said first and second electrically conductive elements are spaced from each other and disposed on opposite sides of said ion-conducting substrate.

11. The potentiometric gas sensor of claim 5 wherein said sensing electrode is constructed of a material selected from a group consisting essentially of platinum, palladium, rhenium, ruthenium, gold, silver, and mixtures or alloys thereof; carbon blacks and carbon fibers; pure metal or metal coated structures, metal such as carbon, metal fibers, or metallic particulate deposited onto support structures; polypyrrole; tungsten, titanium and oxides thereof; organometallic compounds containing elements from the group consisting of cobalt, iron, and nickel; and transition metal complexes containing elements from the Periodic Table of Elements Groups IIIA, IVA, VA, VIA, VIIA, VIIIA, IB, IIB.

12. The potentiometric gas sensor of claim 5 wherein said sensing electrode is an electrode layer constructed of an electrolyte selected from the group comprising an ionic polymer and a solid state electrolyte.

13. The potentiometric gas sensor of claim 5 wherein said sensing electrode is constructed of a material from the group consisting of an ion-conducting polymer, an ion-conducting organic polymer, an ion-conductive solid state electrolyte, and a layer of fiber assemblies.

14. The potentiometric gas sensor of claim 13 wherein said layer of fiber assemblies consist of the catalytic element itself or the catalytic element affixed to a fiber assembly consisting of carbon fibers, carbon black, carbon particulates, metallic fibers, metallic particulates and mixtures thereof coated with a material from the group consisting essentially of platinum, platinum black, palladium, iridium, ruthenium, tungsten, gold, cobalt selenite, platinum/palladium alloy, palladium/rhodium alloy, gold/ruthenium alloy, and compounds containing elements from the group consisting of cobalt, iron, nickel, and transition metal complexes containing elements from the Periodic Table of elements, groups IIIA, IVA, VA, VIA, VIIA, VIIIA, IB, IIB.

15. The potentiometric gas sensor of claim 14 wherein said gas sensing electrode consists of: noble metal catalysts from the group consisting of platinum, palladium, rhenium, ruthenium, gold, silver, and mixtures or alloys thereof; carbon blacks and carbon fibers; carbon, metal fibers, or metallic particulate deposited onto support structures; polypyrrole; tungsten, titanium and oxides thereof; organometallic compounds containing elements from the group consisting of cobalt, iron, and nickel; and transition metal complexes containing elements from the Periodic Table of Elements Groups IIIA, IVA, VA, VIA, VIIA, VIIIA, IB, IIB.

16. The potentiometric gas sensor of claim 5 wherein said reference electrode is selected from a group consisting of silver/silver ion, silver/silver chloride, mercury/mercury chloride, silver/silver halide, mercury/mercury halide, stable metal oxides, stable carbon oxides, and stable redox couples consisting of organic, organometallic, transition metal complexes, and a pH electrode.

17. The potentiometric gas sensor of claim 1 wherein said ion-conducting substrate is selected from the group consisting of an ion-exchange membrane, an ion-conducting polymer, an ion-conducting organic polymer, and a doped ceramic material.

18. The potentiometric gas sensor of claim 17 wherein said ion-exchange membrane is selected from the group of Nafion®, Neosepta®, and Raipore®.

19. The potentiometric gas sensor of claim 18 wherein said ion-conducting polymer is selected from the group consisting of doped polyvinylchloride, polyphenyleneoxide, polyphenyleneglycol, polythiophenes, polypyrrols, polydibenzocrown ethers, polyphenylenes, substituted polyacetylenes, and combinations thereof.

20. The potentiometric gas sensor of claim 19 wherein said ion conductive organic polymer is selected from the group consisting of acid functionality, totally neutralized acid functionalities, partially neutralized acid functionalities, free acid functionality, amine functionalities, totally neutralized amine functionalities, $HSO_4^-$, $HPO_4^{2-}$, carboxylic acid, quaternary ammonium functionalities, and ionically doped polymers.

21. The potentiometric gas sensor of claim 1 wherein said first and second electrically conductive elements are bonded to said ion-conducting substrate.

22. The potentiometric gas sensor of claim 2 wherein said filter layer is mounted to said ion-conducting substrate to enclose said first electrically conductive element between said ion-conducting substrate and said filter layer.

23. A potentiometric gas sensor for detecting the presence of a gas contaminant in a gas sample being monitored, said gas sensor comprising:

a first electrically conductive element which interacts with said gas contaminant present in said gas sample;

a second electrically conductive element which does not interact with said gas contaminant present in said gas sample;

an ionically conductive substrate having said first and second electrically conductive elements mounted thereon;

measuring circuitry connected to said first and second electrically conductive elements; and a filter layer through which said gas being sampled flows prior to being exposed to said first and second electrically conductive elements, said filter layer being a material selected from the group comprising microporous, nanoporous, and non-porous membranes, and chemically reactive materials and wherein said filter layer is constructed of a polymer membrane selected from the group consisting of cationic membranes, anionic membranes, and bipolar membranes.

24. The potentiometric gas sensor of claim 23 wherein said filter layer is a cationic membrane comprised of sulfonic acid groups.

25. The potentiometric gas sensor of claim 22 wherein said filter layer is a porous polymer membrane comprising a molecular sieve dispersed throughout an inert polymeric support.

26. A potentiometric gas sensor for detecting the presence of a gas contaminant in a gas sample being monitored, said gas sensor comprising:

a first electrically conductive element which interacts with said gas contaminant present in said gas sample;

a second electrically conductive element which does not interact with said gas contaminant present in said gas sample;

an ionically conductive substrate having said first and second electrically conductive elements mounted thereon;

measuring circuitry connected to said first and second electrically conductive elements; and a filter layer through which said gas being sampled flows prior to being exposed to said first and second electrically conductive elements, said filter layer being a material selected from the group comprising microporous, nanoporous, and non-porous membranes, and chemically reactive materials and said filter layer is mounted to said ionically conductive substrate to enclose said first electrically conductive element between said ionically conductive substrate and said filter layer and wherein said filter layer is a porous polymer membrane comprising a molecular sieve dispersed throughout an inert polymeric support and wherein said polymer membrane is a nonporous, inert polymeric support having zeolite powder dispersed throughout.

27. The potentiometric gas sensor of claim 26 wherein said zeolite powder is selected from the group consisting of zeolite W, chabazite, erionite, potassium erionite, calcium zeolite A, sodium zeolite A, potassium zeolite A, and lithium zeolite A.

28. A potentiometric gas sensor for detecting the presence of a gas contaminant in a gas sample being monitored, said gas sensor comprising:

a first electrically conductive element which interacts with said gas contaminant present in said gas sample;

a second electrically conductive element which does not interact with said gas contaminant present in said gas sample;

an ionically conductive substrate having said first and second electrically conductive elements mounted thereon;

measuring circuitry connected to said first and second electrically conductive elements; and a filter layer through which said gas being sampled flows prior to being exposed to said first and second electrically conductive elements, said filter layer being a material selected from the group comprising microporous, nanoporous, and non-porous membranes, and chemically reactive materials, and wherein said layer of nanoporous membrane is selected from the group consisting of nanoporous alumina, polysulfone, and regenerated cellulose on a polymeric support.

29. The potentiometric gas sensor of claim 2 wherein said layer of nonporous membrane is selected from the group comprising celulose triacetate, polyesters, vinyl polymers, latex polymer, polysulfone, polyethylene, cellulose, polystyrene, polymethacrylates, polynitriles, polydienes, polyoxides, polyesters, polysiloxanes, polyamides, Nafion®, Teflon®, Kynar®, polypropylene, and tetra polymers, and trifluoro polymers.

30. The potentiometric gas sensor of claim 2 wherein said chemically reactive materials are chemically impregnated substances selected from the group consisting of alumina, carbon, permanganate, silver, copper, high valent chromium, and combinations thereof.

31. The potentiometric gas sensor of claim 1 further including a sensor housing having openings therethrough encasing said first and second electrically conductive elements mounted to said ion-conducting substrate, an alarm device, and interconnecting circuitry.

32. The potentiometric gas sensor of claim 31 wherein said interconnecting circuitry is on a circuit board and said alarm device is a light and a horn.

33. The gas sensor of claim 31 wherein said interconnecting circuitry is connected to a computer.

34. The gas sensor of claim 32 further including said filter mounted within said casing between said openings and said first and second electrically conductive elements.

35. The potentiometric gas sensor of claim 2 wherein said filter material is selected from the group consisting of microporous, nanoporous, permselective, and chemically reactive material.

36. The potentiometric gas sensor of claim 35 wherein said permselective material is a polymer membrane selected from the group consisting of cationic membranes, anionic membranes, and bipolar membranes.

37. A potentiometric gas sensor for detecting the presence of a gas contaminant in a gas sample being monitored, said gas sensor comprising:

a first electrically conductive element which interacts with said gas contaminant present in said gas sample;

a second electrically conductive element which does not interact with said gas contaminant present in said gas sample;

an ionically conductive substrate having said first and second electrically conductive elements mounted thereon;

measuring circuitry connected to said first and second electrically conductive elements; and a filter layer through which said gas being sampled flows prior to being exposed to said first and second electrically conductive elements, said filter layer being a material selected from the group comprising microporous, nanoporous, and non-porous membranes, and chemically reactive materials and said filter material is selected from the group consisting of microporous, nanoporous, permselective, and chemically reactive material wherein said nanoporous material is a membrane selected from the group consisting of nanoporous alumina, polysulfone, and regenerated cellulose on a polymeric support.

38. The potentiometric gas sensor of claim 35 wherein said permselective material is a polymer membrane selected from the group consisting of cationic membranes, anionic membranes, and bipolar membranes.

39. A potentiometric method for sensing the presence of a gas contaminant in a gas sample being monitored comprising the steps of:
  exposing an ion-conducting substrate having first and second electrically conductive elements mounted thereon with said gas sample for ionic conduction between said first and second electrically conductive elements;
  measuring a first voltage signal corresponding to the difference between said first and second electrically conductive electrodes, respectively;
  comparing said first voltage signal with a threshhold voltage signal; and
  outputting a trigger signal indicating the presence of said contaminant gas whenever said first voltage signal is less than said threshhold voltage.

40. The method of claim 39 including the step of removing interference gases from said gas sample prior to exposing said exposing an ion-conducting substrate having first and second electrically conductive electrodes mounted thereon with said gas sample.

41. The method of claim 39 wherein the interterence gases are removed via a gas-selective barrier.

42. The method of claim 39 including the step of displaying the level of said contaminant gas on a meter activated with said trigger signal.

43. The method of claim 39 including the step of actuating an alarm with said trigger signal.

44. The method of claim 39 wherein said contaminant gas is selected from the group comprising carbon monoxide, hydrazine, $H_2S$, hydrocarbons, and alcohols.

45. The method of claim 44 wherein said contaminant gas is carbon monoxide.

46. The gas sensor of claim 1 further including a smoke detector with an alarm device assembled with said ion-conducting substrate having said first and second electrically conductive elements mounted thereon and said voltage measuring circuit connected to said alarm device to activate said alarm device when a contaminant gas is sensed.

47. A multiple layer potentiometric sensor device for detecting the presence of one or more gas contaminants in a gas sample being monitored, comprising:
  a filter layer;
  a first ion-conducting substrate for providing ionic conduction in support of the electronic conduction disposed adjacent said filter layer and having at least one gas sensing electrode mounted to an upper surface of said first ion-conducting substrate, said gas sensing electrode being disposed between said first ion-conducting substrate and said filter layer;
  a second ion-conducting ionically conductive substrate for providing ionic conduction in support of the electronic conduction disposed below said first ion-conducting substrate;
  at least one reference electrode disposed between a lower surface of said first ion-conducting substrate and an upper surface of said second ion-conducting substrate; and
  at least one environmental variable sensing electrode mounted to a lower surface of said second ion-conducting substrate.

48. The multiple layer potentiometric sensor device of claim 47 further including a porous, inert protective layer below said lower surface of said second ion-conducting substrate to cover said environmental variable sensing electrode.

49. The multiple layer potentiometric sensor device of claim 48 wherein said filter layer is a material selected from the group consisting of microporous, nanoporous, permselective, and chemically reactive material.

50. The multiple layer potentiometric sensor device of claim 48 wherein said first and second ion-conducting substrates are selected from the group consisting of an ion-exchange membrane, an ion-conducting polymer, ion-conducting organic polymer, and doped ceramic material.

51. The multiple layer potentiometric sensor device of claim 48 wherein said gas sensing electrode has an output response to a first gas contaminant in said gas sample which is different from the output response of said reference electrode to said first gas contaminant.

52. The multiple layer potentiometric sensor device of claim 51 wherein said gas sensing electrode is constructed with a metal deposited onto a layer of material selected from the group consisting of an ion-exchange membrane, an ion-conducting polymer, an ion-conducting organic polymer, an ion-conductive electrolyte, carbon, and a layer of fiber assemblies.

53. The multiple layer potentiometric sensor device of claim 51 wherein said gas sensing electrode consists of: noble metal catalysts from the group consisting of platinum, palladium, rhenium, ruthenium, gold, silver, and mixtures or alloys thereof; carbon blacks and carbon fibers; carbon, metal fibers, or metallic particulate deposited onto support structures; polypyrrole; tungsten, titanium and oxides thereof; organometallic compounds containing elements from the group consisting of cobalt, iron, and nickel; and transition metal complexes containing elements from the Periodic Table of Elements Groups IIIA, IVA, VA, VIA, VIIA, VIIIA, IB, IIB.

54. The multiple layer potentiometric sensor device of claim 51 wherein said gas sensing electrode is an electrode layer constructed of an electrolyte selected from the group comprising an ionic polymer and a solid state electrolyte.

55. The multiple layer potentiometric sensor device of claim 51 wherein said gas sensing electrode is a material selected from the group consisting of a deposit of metal and ion-conductive electrolyte on a layer of carbon, an electronically conductive polymer, and a layer of fiber assemblies.

56. The multiple layer potentiometric sensor device of claim 51 wherein said reference electrode is selected from a group consisting of silver/silver ion, silver/silver chloride, mercury/mercury chloride, silver/silver halide, mercury/mercury halide, stable metal oxides, stable carbon oxides, and stable redox couples consisting of organic, organometallic, transition metal complexes, and a pH electrode.

57. A multiple layer potentiometric sensor device for detecting the presence of one or more gas contaminants in a gas sample being monitored, comprising:

a filter layer;

a first ionically conductive substrate disposed adjacent said filter layer and having at least one gas sensing electrode mounted to an upper surface of said ionically conductive substrate, said gas sensing electrode being disposed between said first ionically conductive substrate and said filter layer;

a second ionically conductive substrate disposed below said first ionically conductive substrate;

at least one reference electrode disposed between a lower surface of said first ionically conductive substrate and an upper surface of said second ionically conductive substrate; and at least one environmental variable sensing electrode mounted to a lower surface of said second ionically conductive substrate; and a porous, inert protective layer below said lower surface of said second ionically conductive substrate to cover said environmental variable sensing electrode, wherein said porous, inert protective layer is constructed of porous polypropylene or porous polyethylene.

58. A multiple layer potentiometric sensor device for detecting the presence of one or more gas contaminants in a gas sample being monitored, comprising:

a filter layer;

a first ionically conductive substrate disposed adjacent said filter layer and having at least one gas sensing electrode mounted to an upper surface of said ionically conductive substrate, said gas sensing electrode being disposed between said first ionically conductive substrate and said filter layer;

a second ionically conductive substrate disposed below said first ionically conductive substrate;

at least one reference electrode disposed between a lower surface of said first ionically conductive substrate and an upper surface of said second ionically conductive substrate, wherein said at least one environmental variable sensing electrode is a temperature/% RH compensator electrode.

59. The multiple layer potentiometric sensor device of claim 58 wherein said temperature/% RH compensator electrode is a gas diffusion electrode.

60. The multiple layer potentiometric sensor device of claim 58 wherein said at least one environmental variable sensing electrode outputs a voltage signal proportional to changes in both temperature and % RH that is substantially equal to the voltage signal output of said gas sensing electrode in response to variations in both temperature and % RH.

61. The multiple layer potentiometric sensor device of claim 60 wherein said at least one environmental variable sensing electrode does not output a response signal in response to the presence of said gas contaminant for which gas sensing electrode outputs a response signal.

62. A multiple layer potentiometric sensor device for detecting the presence of one or more gas contaminants in a gas sample being monitored, comprising:

a filter layer;

a first ionically conductive substrate disposed adjacent said filter layer and having at least one gas sensing electrode mounted to an upper surface of said ionically conductive substrate, said gas sensing electrode being disposed between said first ionically conductive substrate and said filter layer;

a second ionically conductive substrate disposed below said first ionically conductive substrate;

at least one reference electrode disposed between a lower surface of said first ionically conductive substrate and an upper surface of said second ionically conductive substrate; and a second environmental variable sensing electrode which outputs signals proportional to the pressure of said gas sample.

63. A multiple layer potentiometric sensor device for detecting the presence of one or more gas contaminants in a gas sample being monitored, comprising:

a filter layer;

a first ionically conductive substrate disposed adjacent said filter layer and having at least one gas sensing electrode mounted to an upper surface of said ionically conductive substrate, said gas sensing electrode being disposed between said first ionically conductive substrate and said filter layer;

a second ionically conductive substrate disposed below said first ionically conductive substrate;

at least one reference electrode disposed between a lower surface of said first ionically conductive substrate and an upper surface of said second ionically conductive substrate; and a third environmental variable sensing electrode which outputs signals proportional to the temperature of said gas sample.

64. The multiple layer potentiometric sensor device of claim 47 further including a second gas sensing electrode which has an output response to a second gas contaminant in said gas sample which is different from the output response of said first gas sensing electrode and said reference electrode to said second gas contaminant.

65. The multiple layer potentiometric sensor device of claim 47 wherein said first gas sensing electrode is a carbon monoxide sensing electrode.

66. The multiple layer potentiometric sensor of claim 49 wherein said filter layer is constructed of a polymer membrane selected from the group consisting of cationic membranes, anionic membranes, and bipolar membranes.

67. The multiple layer potentiometric sensor at claim 66 wherein said filter layer is a cationic membrane comprised of sulfonic acid groups.

68. A multiple layer potentiometric sensor device for detecting the presence of one or more gas contaminants in a gas sample being monitored, comprising:

a filter layer;

a first ionically conductive substrate disposed adjacent said filter layer and having at least one gas sensing electrode mounted to an upper surface of said ionically conductive substrate, said gas sensing electrode being disposed between said first ionically conductive substrate and said filter layer;

a second ionically conductive substrate disposed below said first ionically conductive substrate;

at least one reference electrode disposed between a lower surface of said first ionically conductive substrate and an upper surface of said second ionically conductive substrate; and a porous, inert protective layer below said lower surface of said second ionically conductive substrate to cover said environmental variable sensing electrode; and said filter layer is a material selected from the group consisting of microporous, nanoporous, permselective, and chemically reactive material and wherein said filter layer is constructed of a polymer membrane selected from the group consisting of cationic membranes, anionic membranes, and bipolar membranes; and wherein said filter layer is a porous polymer membrane comprising a molecular sieve dispersed throughout an inert polymeric support.

69. The multiple layer potentiometric sensor of claim 66 wherein said polymer membrane is a nonporous, inert polymeric support having zeolite powder dispersed throughout.

70. The multiple layer potentiometric sensor of claim 69 wherein said zeolite powder is selected from the group consisting of zeolite W, chabazite, erionite, potassium erionite, calcium zeolite A, sodium zeolite A, potassium zeolite A, and lithium zeolite A.

71. The multiple layer potentiometric sensor of claim 69 wherein said nonporous, inert polymeric support is a layer of material selected from the group consisting of celulose triacetate, polyesters, vinyl polymers, latex polymer polysulfone, polyethylene, cellulose, polystyrene, polymethacrylates, polynitriles, polydienes, polyoxides, polyesters, polysiloxanes, polyamides, Nafion™, Teflon™, Kynar™, polypropylene, polyethylene, tetra polymers and trifluoro polymers.

72. A multiple layer potentiometric sensor device for detecting the presence of one or more gas contaminants in a gas sample being monitored, comprising:
  a filter layer;
  a first ionically conductive substrate disposed adjacent said filter layer and having at least one gas sensing electrode mounted to an upper surface of said ionically conductive substrate, said gas sensing electrode being disposed between said first ionically conductive substrate and said filter layer;
  a second ionically conductive substrate disposed below said first ionically conductive substrate;
  at least one reference electrode disposed between a lower surface of said first ionically conductive substrate and an upper surface of said second ionically conductive substrate; and a porous, inert protective layer below said lower surface of said second ionically conductive substrate to cover said environmental variable sensing electrode; and
  said filter layer is a material selected from the group consisting of microporous, nanoporous, permselective, and chemically reactive material and said layer of nanoporous material is a membrane selected from the group consisting of nanoporous alumina, polysulfone, and regenerated cellulose on a polymeric support.

73. The multiple layer potentiometric sensor of claim 49 wherein said layer of nonporous membrane is celulose triacetate, polyesters, vinyl polymers, latex polymer polysulfane, polyethylene, cellulose, polystyrene, polymethacrylates, polynitriles, polydienes, polyoxides, polyesters, polysiloxanes, polyamides, Nafion™, Teflon™, Kynar™, polypropylene, polyethylene, tetra fluoro polymer and trifluoro polymer.

74. The multiple layer potentiometric sensor of claim 46 wherein said chemically reactive materials are chemically impregnated substances selected from the group consisting of alumina, carbon, permanganate, silver, copper, high valent chromium, and combinations thereof.

75. A multiple layer potentiometric sensor device for detecting the presence of one or more gas contaminants in a gas sample being monitored, comprising:
  a casing with top and bottom sections and openings through said top section;
  a filter layer disposed in the interior of said casing and dividing said interior into first and second chambers wherein said first chamber includes said top section of said casing and said second chamber includes said bottom section of said casing;
  an ionically conductive substrate disposed in said second chamber and having at least one gas sensing electrode mounted to an upper surface thereof;
  a reference electrode mounted to a lower surface of said ionically conductive substrate whereby said ionically conductive substrate provides ionic conduction between said at least one gas sensing electrode and said reference electrode; and
  at least one environmental variable sensing electrode mounted to said upper surface of said ionically conductive substrate.

76. The multiple layer potentiometric sensor device of claim 75 further including electrical contact members connected to said sensing electrode, said least one environmental variable sensing, and said reference electrode.

77. The multiple layer potentiometric sensor device of claim 75 wherein said ionically conductive substrate is selected from the group consisting of an ion-exchange membrane, an ion-conducting polymer, ion-conducting, organic polymer, and doped ceramic material.

78. The multiple layer potentiometric sensor device of claim 75 wherein said gas sensing electrode has an output response to a gas contaminant in said gas sample which is different from the output response of said reference electrode to said gas contaminant.

79. The multiple layer potentiometric sensor device of claim 78 wherein said gas sensing electrode is a carbon monoxide sensing electrode.

80. The multiple layer potentiometric sensor device of claim 75 wherein said gas sensing electrode is constructed with a metal deposited onto a layer of material selected from the group consisting of an ion-exchange membrane, an ion-conducting polymer, an ion-conducting organic polymer, an ion-conductive electrolyte, carbon, and a layer of fiber assemblies.

81. The multiple layer potentiometric sensor device of claim 75 wherein said gas sensing electrode is constructed of a material selected from a group consisting of: noble metal catalysts from the group consisting of platinum, palladium, rhenium, ruthenium, gold, silver, and mixtures or alloys thereof; carbon blacks and carbon fibers; carbon, metal fibers, or metallic particulate deposited onto support structures; polypyrrole; tungsten, titanium and oxides thereof; organometallic compounds containing elements from the group consisting of cobalt, iron, and nickel; and transition metal complexes containing elements from the Periodic Table of Elements Groups IIIA, IVA, VA, VIA, VIIA, VIIIA, IB, IIB.

82. The multiple layer potentiometric sensor device of claim 75 wherein said gas sensing electrode is an electrode layer constructed of an electrolyte selected from the group consisting of an ionic polymer and a solid state electrolyte.

83. The multiple layer potentiometric sensor device of claim 75 wherein said gas sensing electrode is selected from the group consisting of a deposit of metal and ion-conductive electrolyte on a layer of carbon, an electronically conductive polymer, and a layer of fiber assemblies.

84. The multiple layer potentiometric sensor device of claim 75 wherein said reference electrode is selected from a group consisting of silver/silver ion, silver/silver chloride, mercury/mercury chloride, silver/silver halide, mercury/mercury halide, stable metal oxides, stable carbon oxides, and stable redox couples consisting of organic, organometallic, transition metal complexes, and a pH electrode.

85. A multiple layer potentiometric sensor device for detecting the presence of one or more gas contaminants in a gas sample being monitored, comprising:
- a casing with top and bottom sections and openings through said top section;
- a filter layer disposed in the interior of said casing and dividing said interior into first and second chambers wherein said first chamber includes said top section of said casing and said second chamber includes said bottom section of said casing;
- an ionically conductive substrate disposed in said second chamber and having at least one gas sensing electrode mounted to an upper surface thereof;
- a reference electrode mounted to a lower surface of said ionically conductive substrate; and
- at least one environmental variable sensing electrode mounted to said upper surface of said ionically conductive substrate, said at least one environmental variable sensing electrode is a temperature/% RH compensator electrode.

86. The multiple layer potentiometric sensor device of claim 85 wherein said temperature/% RH compensator electrode is a gas diffusion electrode.

87. The multiple layer potentiometric sensor device of claim 85 wherein said at least one environmental variable sensing electrode outputs a voltage signal proportional to changes in both temperature and % RH that is substantially equal to the voltage signal output of said gas sensing electrode in response to variations in both temperature and % RH.

88. The multiple layer potentiometric sensor device of claim 87 wherein said at least one environmental variable sensing electrode does not output a response signal in response to the presence of said gas contaminant for which gas sensing electrode outputs a response signal.

89. A multiple layer potentiometric sensor device for detecting the presence of one or more gas contaminants in a gas sample being monitored, comprising:
- a casing with top and bottom sections and openings through said top section;
- a filter layer disposed in the interior of said casing and dividing said interior into first and second chambers wherein said first chamber includes said top section of said casing and said second chamber includes said bottom section of said casing;
- an ionically conductive substrate disposed in said second chamber and having at least one gas sensing electrode mounted to an upper surface thereof;
- a reference electrode mounted to a lower surface of said ionically conductive substrate; and
- at least one environmental variable sensing electrode mounted to said upper surface of said ionically conductive substrate,
- said gas sensing electrode is selected from the group consisting of a deposit of metal and ion-conductive electrolyte on a layer of carbon, an electronically conductive polymer, and a layer of fiber assemblies;
- said at least one environmental variable sensing electrode being constructed of the same material from which said gas sensing electrode is constructed; and
- means for isolating said at least one environmental variable sensing electrode from said gas sample in said second chamber.

90. The multiple layer potentiometric sensor device of claim 75 wherein said filter layer is a material selected from the group consisting of microporous, nanoporous, and permselective membranes, and chemically reactive material.

91. The multiple layer potentiometric sensor device of claim 90 wherein said membrane is selected from the group consisting of cationic membranes, anionic membranes, and bipolar membranes.

92. A multiple layer potentiometric sensor device for detecting the presence of one or more gas contaminants in a gas sample being monitored, comprising:
- a casing with top and bottom sections and openings through said top section;
- a filter layer disposed in the interior of said casing and dividing said interior into first and second chambers wherein said first chamber includes said top section of said casing and said second chamber includes said bottom section of said casing;
- an ionically conductive substrate disposed in said second chamber and having at least one gas sensing electrode mounted to an upper surface thereof;
- a reference electrode mounted to a lower surface of said ionically conductive substrate; and
- at least one environmental variable sensing electrode mounted to said upper surface of said ionically conductive substrate, said filter layer is a material selected from the group consisting of microporous, nanoporous and permselective membranes, and chemically reactive material, said membranes are selected from the group consisting of cationic membranes, anionic membranes, and bipolar membranes; and
- wherein said filter layer is a cationic membrane comprised of sulfonic acid groups.

93. The multiple layer potentiometric sensor device of claim 91 wherein said filter layer is a porous polymer membrane comprising a molecular sieve dispersed throughout an inert polymeric support.

94. The multiple layer potentiometric sensor device of claim 91 wherein said polymer membrane is a nonporous, inert polymeric support having zeolite powder dispersed throughout.

95. The multiple layer potentiometric sensor device of claim 94 wherein said zeolite powder is selected from the group consisting of zeolite W, chabazite, erionite, potassium erionite, calcium zeolite A, sodium zeolite A, potassium zeolite A, and lithium zeolite A.

96. The multiple layer potentiometric sensor device of claim 94 wherein said nonporous, inert polymeric support is a layer of material selected from the group consisting of celulose triacetate, polyesters, vinyl polymers, latex polymer polysulfane, polyethylene, cellulose, polystyrene, polymethacrylates, polynitriles, polydienes, polyoxides, polyesters, polysiloxanes, polyamides, Nafion™, Teflon™, Kynar™, polypropylene, polyethylene, tetra polymer and trifluoro polymer.

97. A multiple layer potentiometric sensor device for detecting the presence of one or more gas contaminants in a gas sample being monitored, comprising:
- a casing with top and bottom sections and openings through said top section;
- a filter layer disposed in the interior of said casing and dividing said interior into first and second chambers wherein said first chamber includes said top section of said casing and said second chamber includes said bottom section of said casing;
- an ionically conductive substrate disposed in said second chamber and having at least one gas sensing electrode mounted to an upper surface thereof;

a reference electrode mounted to a lower surface of said ionically conductive substrate; and at least one environmental variable sensing electrode mounted to said upper surface of said ionically conductive substrate, said filter layer is a material selected from the group consisting of microporous, nanoporous, and permselective membranes, and chemically reactive material; said layer of nanoporous membranes is a membrane selected from the group consisting of nanoporous alumina, polysulfone, and regenerated cellulose on a polymeric support.

98. The multiple layer potentiometric sensor device of claim 90 wherein said layer of nonporous membrane is celulose triacetate, polyesters, vinyl polymers, latex polymer polysulfane, polyethylene, cellulose, polystyrene, polymethacrylates, polynitriles, polydienes, polyoxides, polyesters, polysiloxanes, polyamides, Nafion™, Teflon™, Kynar™, polypropylene, polyethylene, tetra polymer and trifluoro polymer.

99. The multiple layer potentiometric sensor device of claim 90 wherein said chemically reactive materials are chemically impregnated substances selected from the group consisting of alumina, carbon, permanganate, silver, copper, high valent chromium, and combinations thereof.

100. The multiple layer potentiometric sensor device of claim 90 wherein said filter layer is a cup shaped support containing said chemically reactive material.

101. A multiple layer potentiometric sensor device for detecting the presence of one or more gas contaminants in a gas sample being monitored, comprising:

a casing with top and bottom sections and openings through said top section;

a filter layer disposed in the interior of said casing and dividing said interior into first and second chambers wherein said first chamber includes said top section of said casing and said second chamber includes said bottom section of said casing;

an ionically conductive substrate disposed in said second chamber and having at least one gas sensing electrode mounted to an upper surface thereof;

a reference electrode mounted to a lower surface of said ionically conductive substrate; and at least one environmental variable sensing electrode mounted to said upper surface of said ionically conductive substrate, said filter layer is a material selected from the group consisting of microporous, nanoporous, and permselective membranes, and chemically reactive material; and said filter layer is a cup shaped support containing said chemically reactive material and said cup shaped support has a meshed bottom surface and support sides extending outward from said cup support and attached to said casing to divide said casing into said first and second chambers.

102. A method for detecting the presence of one or more gas contaminants in a gas sample being monitored, comprising the steps of:

directing said gas sample across a filter layer disposed in the interior of a casing to remove any interference gas from said gas sample;

exposing an ionically conductive substrate having at least one gas sensing electrode and at least one environmental variable sensing electrode mounted to one surface thereof and a reference electrode mounted to a different surface thereof to said gas sample subsequent to the removal of said interference gas;

compensating for changes in at least one environmental variable by subtracting a function of first voltage signal output by said at least one gas sensing electrode from a second voltage signal output by said at least one environmental variable sensing electrode to generate a compensated voltage signal output;

generating a third voltage signal corresponding to the difference between said compensated voltage signal output;

comparing said third voltage signal with a reference signal; and generating a trigger signal indicating the presence of said contaminant gas whenever said third voltage signal is less than said reference signal.

103. The method of claim 102 including the step of detecting the presence of one or more gas contaminants selected from the group consisting of carbon monoxide, hydrazine, $H_2S$, hydrocarbons, and alcohols.

104. The method of claim 103 including the step of activating an alarm with said trigger signal whenever said one or more gas contaminants are detected.

105. The method of claim 103 wherein said contaminant gas is carbon monoxide.

106. The method of claim 104 including the step of generating a second voltage signal output by said at least one environmental variable sensing electrode corresponding to changes in temperature and % RH.

107. A multiple layer potentiometric sensor device for detecting the presence of one or more gas contaminants in a gas sample being monitored, comprising:

a casing with top and bottom section and openings through said top section into an interior of said casing;

a chemical filter material dispersed throughout interior of said casing;

an ionically conductive substrate disposed in said interior and having at least one gas sensing electrode mounted to an upper surface thereof;

a reference electrode mounted to a lower surface of said ionically conductive substrate whereby said ionically conductive substrate provides ionic conduction in support of the electronic conduction between said at least one gas sensing electrode and said reference electrode; and at least one environmental variable sensing electrode mounted to the upper surface of said ionically conductive substrate.

108. The multiple layer potentiometric sensor device of claim 107 further including electrical contact members connected to said gas sensing electrode, said least one environmental variable sensing, and said reference electrode.

109. The multiple layer potentiometric sensor device of claim 107 wherein said ionically conductive substrate is selected from the group consisting of an ion-exchange membrane, an ion-conducting polymer, ion-conducting, organic polymer, and doped ceramic material.

110. The multiple layer potentiometric sensor device of claim 107 wherein said gas sensing electrode has an output response to a gas contaminant in said gas sample which is different from the output response of said reference electrode to said gas contaminant.

111. The multiple layer potentiometric sensor device of claim 110 wherein said gas sensing electrode is a carbon monoxide sensing electrode.

112. The multiple layer potentiometric sensor device of claim 107 wherein said gas sensing electrode is constructed with a metal deposited onto a layer of material selected from the group consisting of an ion-exchange membrane, an ion-conducting polymer, an ion-conducting organic polymer, an ion-conductive electrolyte, carbon, and a layer of fiber assemblies.

113. The multiple layer potentiometric sensor device of claim 107 wherein said gas sensing electrode is constructed of a material selected from a group consisting essentially of platinum, ruthenium, tungsten, tungstenates, carbon black, carbon fibers, carbon particulates, electrically conductive polymers, metallic particulates, or mixtures thereof coated with a material from the group consisting essentially of platinum, platinum black palladium, iridium, gold, cobalt selenite, platinum/palladium alloy, platinum/ruthem alloy palladium/rhodium alloy, gold/ruthenium alloy, and organometallic compounds containing elements from the group consisting of cobalt, iron and nickel, and transition metal complexes containing elements from the Periodic Table of elements: groups IIIA, IVA, VA, VIA, VIIA, VIIIA, IB, IIB.

114. The multiple layer potentiometric sensor device of claim 107 wherein said gas sensing electrode is an electrode layer constructed of an electrolyte selected from the group consisting of an ionic polymer and a solid state electrolyte.

115. The multiple layer potentiometric sensor device of claim 107 wherein said gas sensing electrode is constructed of a deposit of metal and ion-conductive electrolyte on a layer of carbon, an electronically conductive polymer, or a layer of fiber assemblies.

116. The multiple layer potentiometric sensor device of claim 107 wherein said reference electrode is selected from a group consisting essentially of silver/silver ion, silver/silver chloride, mercury/mercury chloride, silver/silver halide, mercury/mercury halide, stable metal oxides, stable carbon oxides, and stable redox couples consisting of organic, organometallic, transition metal complexes, and a pH electrode.

117. A multiple layer potentiometric sensor device for detecting the presence of one or more gas contaminants in a gas sample being monitored, comprising:
   a casing with top and bottom section and openings through said top section into an interior of said casing;
   a chemical filter material dispersed throughout interior of said casing;
   an ionically conductive substrate disposed in said interior and having at least one gas sensing electrode mounted to an upper surface thereof;
   a reference electrode mounted to a lower surface of said ionically conductive substrate; and
   at least one environmental variable sensing electrode mounted to the upper surface of said ionically conductive substrate, said at least one environmental variable sensing electrode is a temperature/% RH compensator electrode.

118. A multiple layer potentiometric sensor device for detecting the presence of one or more gas contaminants in a gas sample being monitored, comprising:
   a casing with top and bottom section and openings through said top section into an interior of said casing;
   a chemical filter material dispersed throughout interior of said casing;
   an ionically conductive substrate disposed in said interior and having at least one gas sensing electrode mounted to an upper surface thereof;
   a reference electrode mounted to a lower surface of said ionically conductive substrate; and
   at least one environmental variable sensing electrode mounted to the upper surface of said ionically conductive substrate, said temperature/% RH compensator electrode is a gas diffusion electrode.

119. A multiple layer potentiometric sensor device for detecting the presence of one or more gas contaminants in a gas sample being monitored, comprising:
   a casing with top and bottom section and openings through said top section into an interior of said casing;
   a chemical filter material dispersed throughout interior of said casing;
   an ionically conductive substrate disposed in said interior and having at least one gas sensing electrode mounted to an upper surface thereof;
   a reference electrode mounted to a lower surface of said ionically conductive substrate; and
   at least one environmental variable sensing electrode mounted to the upper surface of said ionically conductive substrate, said at least one environmental variable sensing electrode outputs a voltage signal proportional to changes in both temperature and % RH that is substantially equal to the voltage signal output of said gas sensing electrode in response to variations in both temperature and % RH.

120. The multiple layer potentiometric sensor device of claim 117 wherein said at least one environmental variable sensing electrode does not output a response signal in response to the presence of said gas contaminant for which gas sensing electrode outputs a response signal.

121. The multiple layer potentiometric sensor device of claim 117 wherein:
   said at least one environmental variable sensing electrode is constructed of the same material from which said gas sensing electrode is constructed; and
   means for isolating said at least one environmental variable sensing electrode from said gas sample in said second chamber.

\* \* \* \* \*